(12) United States Patent
Holland et al.

(10) Patent No.: US 12,049,452 B2
(45) Date of Patent: Jul. 30, 2024

(54) OLAPARIB HYDROXYBENZOIC ACID COCRYSTALS AND THEIR PHARMACEUTICAL USE

(71) Applicant: NUFORMIX TECHNOLOGIES LIMITED, London (GB)

(72) Inventors: Joanne Holland, Cambridge (GB); Alex Eberlin, Cambridge (GB)

(73) Assignee: NUFORMIX TECHNOLOGIES LIMITED, London (GB)

( * ) Notice: Subject to any disclaimer, the term of this patent is extended or adjusted under 35 U.S.C. 154(b) by 0 days.

(21) Appl. No.: 18/054,272

(22) Filed: Nov. 10, 2022

(65) Prior Publication Data
US 2023/0183185 A1 Jun. 15, 2023

Related U.S. Application Data

(60) Provisional application No. 63/277,773, filed on Nov. 10, 2021.

(51) Int. Cl.
*C07D 237/32* (2006.01)
*C07C 65/03* (2006.01)
*C07C 65/05* (2006.01)
*C07C 65/10* (2006.01)

(52) U.S. Cl.
CPC ............ *C07D 237/32* (2013.01); *C07C 65/03* (2013.01); *C07C 65/05* (2013.01); *C07C 65/10* (2013.01); *C07B 2200/13* (2013.01)

(58) Field of Classification Search
CPC .......................... C07D 237/32; C07B 2200/13
See application file for complete search history.

(56) References Cited

U.S. PATENT DOCUMENTS

2023/0322686 A1* 10/2023 Holland .................. A61P 35/00
514/248

FOREIGN PATENT DOCUMENTS

| CN | 105753789 A | * | 7/2016 | |
| CN | 111689905 A | * | 9/2020 | ............ A61P 35/00 |
| CN | 111825621 A | * | 10/2020 | |
| CN | 111995582 A | * | 11/2020 | ............ A61P 35/00 |
| CN | 113636979 A | * | 11/2021 | |
| WO | 2021044437 A1 | | 3/2021 | |
| WO | WO-2022058785 A1 | * | 3/2022 | |

OTHER PUBLICATIONS

Brittain; Cryst. Growth Des. 2012, 12, 2, 1046-1054. https://doi.org/10.1021/cg201510n (Year: 2012).*
Karimi-Jafari; Crystal Growth & Design 2018, 18, 6370-6387. https://doi.org/10.1021/acs.cgd.8b00933 (Year: 2018).*
Buddhadev; Proceedings 2020, 62, 14. https://doi.org/10.3390/proceedings2020062014 (Year: 2020).*
Yang; CrystEngComm, 2020,22, 5628-5637. https://doi.org/10.1039/D0CE00833H (Year: 2020).*
Guo; Acta Pharmaceutica Sinica B 2021, 11, 2537-2564. https://doi.org/10.1016/j.apsb.2021.03.030 (Year: 2021).*
International Search Report and Written Opinion of PCT International Application No. PCT/IB2022/000711 filed Nov. 10, 2022, dated Apr. 6, 2023.

* cited by examiner

*Primary Examiner* — Daniel R Carcanague
(74) *Attorney, Agent, or Firm* — RAPHAEL BELLUM PLLC

(57) ABSTRACT

The invention relates to new 1:1 olaparib:hydroxybenzoic acid cocrystals. The invention also relates to new 2:1 olaparib:hydroxybenzoic acid cocrystals which may contain no water (anhydrous) or may optionally be hydrated. The invention also relates to pharmaceutical compositions containing an olaparib hydroxybenzoic acid cocrystal of the invention and a pharmaceutically acceptable carrier. The olaparib hydroxybenzoic acid cocrystals of the invention may be useful for the treatment of diseases that benefit from inhibition of poly (ADP-ribose) polymerase (PARP).

33 Claims, 32 Drawing Sheets

OLAPARIB HYDROXYBENZOIC ACID COCRYSTALS AND THEIR PHARMACEUTICAL USE

CROSS-REFERENCE TO RELATED APPLICATIONS

This application claims priority to U.S. Provisional Application No. 63/277,773, filed on Nov. 10, 2021, the disclosure of which is incorporated by reference.

TECHNICAL FIELD

This disclosure relates to olaparib hydroxybenzoic acid cocrystals, therapeutic uses of the cocrystals and pharmaceutical compositions containing them.

BACKGROUND

Olaparib, (4-[(3-{[4-(cyclopropylcarbonyl)piperazin-1-yl]carbonyl}-4-fluorophenyl)methyl]phthalazin-1(2H)-one, shown below), is an inhibitor of the enzyme poly (ADP-ribose) polymerase (PARP). Its synthesis was first described in WO2004080976.

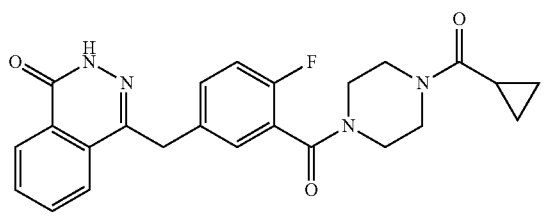 [SMILES: O=C(c1cc(Cc2n[nH]c(=O)c3ccccc23)ccc1F)N1CCN(C(=O)C2CC2)CC1]

Olaparib is currently marketed by AstraZeneca, under the Lynparza® brand name for the treatment of adults with suspected deleterious germline or somatic BRCA gene mutated ovarian, breast, or pancreatic cancer, or for suspected deleterious germline or somatic homologous recombination repair (HRR) gene mutated prostate cancer.

As described by the European Medicines Agency CHMP assessment report (EMA/CHMP/789139/2014) olaparib is classified by the Biopharmaceutical Classification System (BCS) as being a class 4 drug meaning it has both low solubility and low permeability. To enable sufficient efficacy, it is therefore critical to find forms of olaparib with the highest possible solubility and bioavailability. Olaparib exists in multiple polymorphic forms, as well as solvated and hydrated forms, which have been disclosed, for example, in WO2008/04708 (Form A), WO2009/050469 (Form L), WO2010/041051, WO2017/123156, and WO2017/40283. The original marketed formulation contained Form A which has pH independent aqueous solubility of ~0.1 mg/ml. As the polymorphic crystalline forms of olaparib have such low solubility, a solubility enhancing formulation was required to achieve sufficient bioavailability. The original marketed formulation was a capsule, where olaparib Form A was micronised and formulated as a crystalline dispersion in the semi-solid Lauroyl macrogolglyceride (LMG) matrix. This formulation improved the bioavailability of pure crystalline olaparib, however, due to the amount of LMG needed in the formulation only 50 mg capsules were possible. Clinical trials showed the efficacious dose of olaparib to be 400 mg twice daily resulting in patients requiring 16 capsules per day. Also due to the amount of excipient needed, the capsules were of a large size (size 0). It was also found that different polymorphic forms of olaparib can arise even when using the same solvent or solvent mixture. For example, WO2009/050469 and WO2008/04708 demonstrate that both ethanol/water and methanol/water can afford both Form A and Form L (both anhydrous forms) whereas water alone produces olaparib hydrate (Form H). Also, different solvents can lead to different solvated forms and mixed solvents can lead to mixed solvates of differing ratios (WO2017/40283). It is therefore difficult to control the precise form of olaparib that is produced using a specific method. In 2018 AstraZeneca had to recall a batch of olaparib capsules as they were found to contain levels of Form L above the specified limit. They also recalled several other batches for fear that amounts of Form L may increase during the shelf life of the capsules. There is therefore a need for new crystalline forms of olaparib that do not exist in multiple polymorphic forms and that do not convert form on storage or produce solvated or hydrated forms.

More recently a new tablet formulation has been developed to overcome some of these limitations. The tablet formulation contains an amorphous solid dispersion of olaparib in a matrix with copovidone polymer, formed using a melt extrusion method. This new tablet formulation showed faster dissolution compared to the capsule formulation and subsequently higher bioavailability, resulting in the daily dose of olaparib being lowered from 800 mg to 600 mg. Use of an amorphous form of olaparib also overcame the issue of polymorph conversion, although this approach brings a number of disadvantages: 1) amorphous forms, being metastable, are generally less stable than crystalline forms in terms of storage, therefore requiring large amounts of stabiliser to maintain the amorphous form; 2) amorphous forms always carry the risk of re-crystallisation on storage; and 3) as the polymer (copovidone) used in the tablet matrix is hygroscopic, the tablet formulation requires protective packaging to prevent moisture uptake. It would therefore be preferable to find an alternative crystalline form of olaparib that could provide higher solubility, like an amorphous form, but without the inherent poor stability of amorphous forms and without the need for a stabilising agent.

Over recent years it has been found that the enzyme PARP plays a key role in multiple non-oncological diseases (C. Szabo et al., *B. J. Pharm.* (2018) 175:1932-222). PARP has been shown to be associated with pulmonary inflammatory diseases such as asthma, COPD, and acute lung injury (ALI) as well as other inflammatory conditions such as arthritis and colitis. It has also been found to be a major contributing factor in neurodegenerative diseases such as Parkinson's and Alzheimer's diseases, in cardiovascular conditions such as myocardial ischemia/reperfusion injury, various forms of heart failure, cardiomyopathies, circulatory shock, cardiovascular aging, diabetic cardiovascular complications, myocardial hypertrophy, atherosclerosis, vascular remodelling following injury and atherosclerosis. PARP has been implicated in several ophthalmic diseases such as retinal degeneration, retinal or optic nerve disease, and glaucoma (U.S. Pat. No. 6,444,676). PARP has been shown to be a key mediating factor in the progression of multiple types of fibrosis including lung, cardiac, liver, and renal fibrosis. This would suggest that olaparib could be used to treat numerous non-oncology conditions.

However, orally-delivered olaparib has multiple tolerability side effects that can often be severe including nausea, vomiting, fatigue, and anaemia. Development of alternative delivery methods that would allow local delivery of olaparib to enable treatment of disease with minimal systemic exposure could allow olaparib to be repurposed for new diseases with lower risk of side effects, potentially increasing patient compliance. Also given the wide range of diseases for which olaparib could have a potential therapeutic benefit, as well as the different patient types and specific areas of the body requiring treatment, it is anticipated that patients would benefit from having multiple delivery methods for the administration of olaparib so as to best suit the patient's needs. The pharmaceutical compositions could include, for example, an orally inhalable composition, an ophthalmic composition, a topical composition, or a transdermal composition. For example, an inhaled formulation could allow treatment of lung diseases such as lung fibrosis, asthma, COPD, and ALI without the side effects of oral delivery. However, amorphous drug forms that require large amounts of stabilising polymer and are hygroscopic, or crystalline forms subject to polymorphic instability, are not suitable for inhaled delivery. Alternatively, the low solubility of the known crystalline forms of olaparib would not enable ophthalmic or dermal formulation. There is, therefore, a need for new crystalline forms of olaparib with both good stability and increased solubility to enable alternative formulations of olaparib to treat novel PARP mediated diseases.

The most common alternative crystalline form used to improve the solubility of a low solubility drug is a pharmaceutically acceptable salt. A crystalline salt is formed when the drug and a second component are crystallized together to form a two-component crystalline complex, held together through ionic bonding, with proton transfer occurring between the two components. A drug salt will often have superior physical properties compared to the pure crystalline drug. However, olaparib is non-ionisable, so it cannot form salts. For non-ionisable drugs, formation of a cocrystal is an alternative two-component crystalline complex where the drug and a second component are held together through non-ionic bonds such as hydrogen bonds or Van der Waals bonds with no proton exchange occurring between the two components. The second component in a cocrystal is termed a 'coformer'. Drug cocrystals have unique crystalline structures with distinct crystallographic and spectroscopic properties compared to the drug and coformer individually. These multi-component assemblies are continuing to excite and find usefulness, particularly within the pharmaceutical field, as drug cocrystals often possess more favourable pharmaceutical properties compared to the pure drug, often making them more suitable for new drug delivery options not possible with either the pure crystalline drug or its amorphous form. This is because a cocrystal form may have improved properties, for example, improved dissolution or solubility properties, or advantageous storage stability, melting point, hygroscopicity, or other physico-chemical properties. For a pharmaceutical cocrystal of olaparib to be acceptable as an alternative marketed form of olaparib it is important that the coformer used is 'inactive' and that it is accepted from a regulatory perspective for use in a pharmaceutical formulation. A 1:1 olaparib urea cocrystal has previously been disclosed in CN 105753789. However, as this patent only discloses one cocrystal of olaparib, there remains, therefore, a need for other pharmaceutically acceptable olaparib cocrystals with an even greater improvement in dissolution rate and lower hygroscopicity. A 1:1 olaparib fumaric acid cocrystal and a 1:1 olaparib 3,5-dihydroxybenzoic acid cocrystal have previously been disclosed in WO 2021/044437; a 1:1 olaparib maleic acid cocrystal has previously been disclosed in CN 111689905; and a 1:1 olaparib malonic acid cocrystal has previously been disclosed in CN 111825621. However, these cocrystals could not be reproduced with the methods disclosed therein.

SUMMARY

The invention relates to new 1:1 olaparib:hydroxybenzoic acid cocrystals, wherein the hydroxybenzoic acid of the 1:1 olaparib:hydroxybenzoic acid cocrystals is a compound of formula (I):

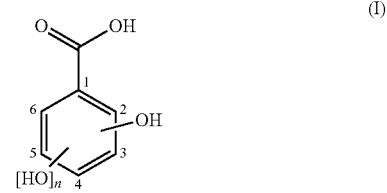

wherein n=0 or 1;
with the proviso that when n=1, the hydroxyl groups are not at the 3-position and the 5-position of the benzene ring.

The invention also relates to new 2:1 olaparib:hydroxybenzoic acid cocrystals, wherein the hydroxybenzoic acid of the 2:1 olaparib:hydroxybenzoic acid cocrystals is a compound of formula (II):

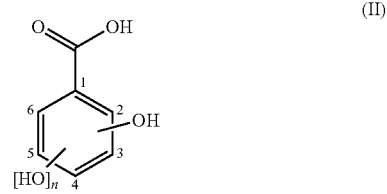

wherein n=0 or 1.

The 2:1 olaparib:hydroxybenzoic acid cocrystals may contain no water (anhydrous) or may optionally be hydrated. The 2:1 olaparib:hydroxybenzoic acid cocrystals may, depending on conditions, such as humidity, contain varying amounts of water, typically an average of up to about three waters of hydration.

For example, in the 2:1 olaparib:hydroxybenzoic acid cocrystals of the invention, the cocrystal may contain up to about one water of hydration, up to about two waters of hydration, up to about three waters of hydration, or an average number of waters of hydration.

Exemplary hydroxybenzoic acid coformers may include gentisic acid, 2,4-dihydroxbenzoic acid, 4-hydroxybenzoic acid, salicylic acid, or 3,4-dihydroxybenzoic acid.

In particular, the olaparib hydroxybenzoic acid cocrystals of the invention relate to a 1:1 olaparib gentisic acid cocrystal, a 2:1 olaparib gentisic acid cocrystal, a 1:1 olaparib 2,4-dihydroxybenzoic acid cocrystal, a 2:1 olaparib 2,4-dihydroxybenzoic acid cocrystal, a 2:1 olaparib 4-hydroxybenzoic acid cocrystal, a 1:1 olaparib salicylic acid cocrystal, and a 1:1 olaparib 3,4-dihydroxybenzoic acid cocrystal.

The invention also relates to pharmaceutical compositions containing an olaparib hydroxybenzoic acid cocrystal of the invention and a pharmaceutically acceptable carrier. The olaparib hydroxybenzoic acid cocrystals of the invention may be used in the same way as olaparib. Olaparib is useful in treating diseases that benefit from inhibition of poly (ADP-ribose) polymerase (PARP). These include cancer, fibrosis, inflammatory conditions (e.g., asthma, COPD, colitis, arthritis), neurological diseases (e.g., neurodegeneration, neurotrauma, stroke), cardiovascular conditions, ophthalmic degenerative diseases, vascular diseases (e.g., diabetic complications, atherosclerosis), and various forms of critical illness (e.g., septic shock, ALI, acute liver failure). The olaparib hydroxybenzoic acid cocrystals of the invention may, therefore, be useful for the treatment of such diseases, disorders, and conditions.

DETAILED DESCRIPTION

The invention relates to new 1:1 olaparib:hydroxybenzoic acid cocrystals, wherein the hydroxybenzoic acid of the 1:1 olaparib:hydroxybenzoic acid cocrystals is a compound of formula (I):

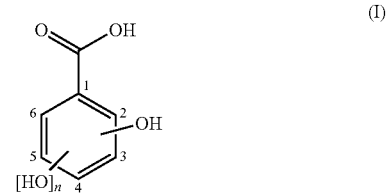

(I)

wherein n=0 or 1;
with the proviso that when n=1, the hydroxyl groups are not at the 3-position and the 5-position of the benzene ring.
The invention also relates to new 2:1 olaparib:hydroxybenzoic acid cocrystals, wherein the hydroxybenzoic acid of the 2:1 olaparib:hydroxybenzoic acid cocrystals is a compound of formula (II):

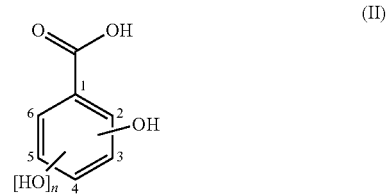

(II)

wherein n=0 or 1.
The 2:1 olaparib:hydroxybenzoic acid cocrystals may contain no water (anhydrous) or may optionally be hydrated. The 2:1 olaparib:hydroxybenzoic acid cocrystals may, depending on conditions, such as humidity, contain varying amounts of water, typically an average of up to about three waters of hydration.
For example, in the 2:1 olaparib:hydroxybenzoic acid cocrystals of the invention, the cocrystal may contain up to about one water of hydration, up to about two waters of hydration, up to about three waters of hydration, or an average number of waters of hydration.

Exemplary hydroxybenzoic acid coformers may include gentisic acid, 2,4-dihydroxbenzoic acid, 4-hydroxybenzoic acid, salicylic acid, or 3,4-dihydroxybenzoic acid.

In particular, the olaparib hydroxybenzoic acid cocrystals of the invention relate to a 1:1 olaparib gentisic acid cocrystal, a 2:1 olaparib gentisic acid cocrystal, a 1:1 olaparib 2,4-dihydroxybenzoic acid cocrystal, a 2:1 olaparib 2,4-dihydroxybenzoic acid cocrystal, a 2:1 olaparib 4-hydroxybenzoic acid cocrystal, a 1:1 olaparib salicylic acid cocrystal, and a 1:1 olaparib 3,4-dihydroxybenzoic acid cocrystal.

Figure 32:
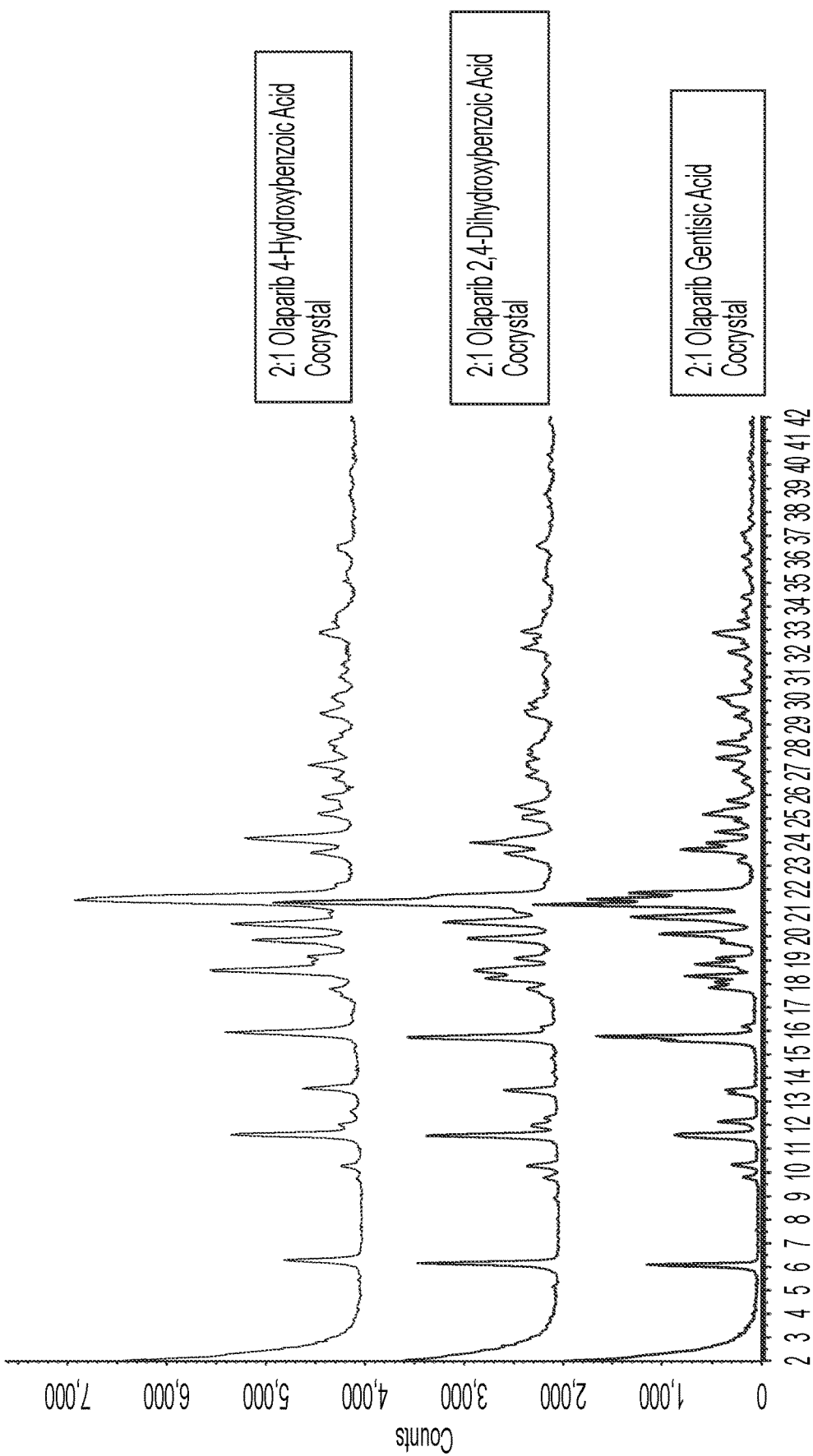
FIG. 32 shows an XRPD overlay of the 2:1 olaparib gentisic acid cocrystal, the 2:1 2,4-dihydroxybenzoic acid cocrystal, and the 2:1 olaparib 4-hydroxybenzoic acid cocrystal.

The 2:1 olaparib:hydroxybenzoic acid cocrystals of the invention are uniquely isostructural. The 2:1 olaparib:hydroxybenzoic acid cocrystals of the invention are characterized by common peaks of a powder X-ray diffraction pattern, wherein at least two, at least three, at least four, or all of the peaks are selected from the peaks at 6.2, 10.3, 11.6, 13.5, and 17.8°2θ±0.2°2θ. The 2:1 olaparib:hydroxybenzoic acid cocrystals of the invention are characterized by a powder X-ray diffraction pattern substantially similar to FIG. 5, 14, or 19. The common peaks of the 2:1 olaparib:hydroxybenzoic acid cocrystals of the invention are depicted in FIG. 32 showing an overlay of the powder X-ray diffraction patterns.

The 2:1 olaparib:hydroxybenzoic acid cocrystals of the invention are characterized by common peaks of an Infrared Spectrum, wherein at least two, at least three, at least four, or all of the peaks are selected from the peaks at 1014, 1222, 1243, 1435, and 1590 $cm^{-1}\pm 1$ $cm^{-1}$. The 2:1 olaparib:hydroxybenzoic acid cocrystals of the invention are characterized by an Infrared Spectrum substantially similar to FIG. 8, 17, or 22.

These olaparib hydroxybenzoic acid cocrystals of the invention, their preparation, and their characterization are described in the examples below and shown in the figures. The invention relates to pharmaceutical compositions containing a therapeutically effective amount of an olaparib hydroxybenzoic acid cocrystal of the invention and one or more pharmaceutically acceptable carriers. The invention also relates to methods of treatment for the diseases, disorders, and conditions described herein and the use of a therapeutically effective amount of an olaparib hydroxybenzoic acid cocrystal of the invention, or a pharmaceutical composition containing it, for that treatment. The invention further provides the use of an olaparib hydroxybenzoic acid cocrystal of the invention in the manufacture of a medicament for use in the treatment of the diseases, disorders, and conditions described herein.

Therapeutic Uses of Olaparib Hydroxybenzoic Acid Cocrystals

As discussed above olaparib is known in the art to be useful in the treatment of various diseases, disorders, and conditions. The olaparib hydroxybenzoic acid cocrystals of the invention, 1:1 olaparib gentisic acid cocrystal, 2:1 olaparib gentisic acid cocrystal, 1:1 olaparib 2,4-dihydroxybenzoic acid cocrystal, 2:1 olaparib 2,4-dihydroxybenzoic acid cocrystal, 2:1 olaparib 4-hydroxybenzoic acid cocrystal, 1:1 olaparib salicylic acid cocrystal, and 1:1 olaparib 3,4-dihydroxybenzoic acid cocrystal, and pharmaceutical compositions containing them may then also be used to treat such diseases, disorders, and conditions. The diseases, disorders, or conditions which may be treated with an olaparib hydroxybenzoic acid cocrystal of the invention include, but are not limited to: cancer, fibrosis, inflammatory conditions (e.g., asthma, COPD, colitis, arthritis), neurological diseases (e.g., neurodegeneration, neurotrauma, stroke), cardiovascular conditions, ophthalmic degenerative diseases, vascular diseases (e.g., diabetic complications, atherosclerosis), and various forms of critical illness (e.g., septic shock, ALI, acute liver failure).

Accordingly, the invention relates to the method of treating such a disease, disorder, or condition comprising the step of administering to a patient in need thereof a therapeutically effective amount of an olaparib hydroxybenzoic acid cocrystal of the invention or of administering to a patient in need thereof a therapeutic composition containing an olaparib hydroxybenzoic acid cocrystal of the invention.

The term "treatment" or "treating" means any treatment of a disease, disorder, or condition in a mammal, including: preventing or protecting against the disease, disorder, or condition, that is, causing the clinical symptoms not to develop; inhibiting the disease, disorder, or condition, that is, arresting or suppressing the development of clinical symptoms; and/or relieving the disease, disorder, or condition (including the relief of discomfort associated with the condition or disorder), that is, causing the regression of clinical symptoms. It will be understood by those skilled in the art that in human medicine, it is not always possible to distinguish between "preventing" and "suppressing" since the ultimate inductive event or events may be unknown, latent, or the patient is not ascertained until well after the occurrence of the event or events. Therefore, as used herein the term "prophylaxis" is intended as an element of "treatment" to encompass both "preventing" and "suppressing" the disease, disorder, or condition. The term "protection" is meant to include "prophylaxis."

Another aspect of the invention relates to the use of an olaparib hydroxybenzoic acid cocrystal of the invention in the treatment of diseases, disorders, and conditions discussed above. Accordingly, the invention further relates to the manufacture of a medicament for use in the treatment of such diseases, disorders, and conditions.

Pharmaceutical Compositions Containing Olaparib Hydroxybenzoic Acid Cocrystals

The invention relates to pharmaceutical compositions comprising, consisting essentially, or consisting of a therapeutically effective amount of an olaparib hydroxybenzoic acid cocrystal of the invention and a pharmaceutically acceptable carrier (also known as a pharmaceutically acceptable excipient). As mentioned above, these pharmaceutical compositions are therapeutically useful to treat or prevent disorders such as those discussed above. A pharmaceutical composition of the invention may be a solid dosage form, or a liquid formulation made with an olaparib hydroxybenzoic acid cocrystal of the invention.

A pharmaceutical composition of the invention may be in any pharmaceutical form which contains an olaparib hydroxybenzoic acid cocrystal of the invention. The pharmaceutical composition may be, for example, a tablet, a capsule, an oral solution, an injectable composition, a topical composition, an inhalable composition, or a transdermal composition. Liquid pharmaceutical compositions may be prepared using an olaparib hydroxybenzoic acid cocrystal of the invention and represent a particular embodiment of the invention. For a liquid pharmaceutical composition, the olaparib hydroxybenzoic acid cocrystal of the invention may be dissolved in a solvent, e.g., water, and provided to the patient as a solution or provided as a dry form for preparation into a solution at the time and point of care.

The pharmaceutical compositions generally contain, for example, about 0.1% to about 99.9% by weight of an olaparib hydroxybenzoic acid cocrystal of the invention, for example, about 0.5% to about 99.5% by weight of an olaparib hydroxybenzoic acid cocrystal of the invention and, for example, 99.5% to 0.5% by weight of at least one suitable pharmaceutical excipient or solvent. In one embodiment, the composition may be between about 5% and about 75% by weight of an olaparib hydroxybenzoic acid cocrystal of the invention with the rest being at least one suitable pharmaceutical excipient, solvent, or at least one other adjuvant, as discussed below.

A "therapeutically effective amount of an olaparib hydroxybenzoic acid cocrystal of the invention" is that which correlates to a therapeutic effect and may, for example, be about 5 mg to about 2,000 mg, about 50 mg to about 1500 mg, about 100 mg to about 1000 mg, about 250 mg to about 750 mg, or about 500 mg. The actual amount required for treatment of any particular disease, disorder, or condition for any particular patient may depend upon a variety of factors including, for example, the particular disease, disorder, or condition being treated; the disease state being treated and its severity; the specific pharmaceutical composition employed; the age, body weight, general health, sex, and diet of the patient; the mode of administration; the time of administration; the route of administration; the rate of excretion; the duration of the treatment; any drugs used in combination or coincidental with the specific compound employed; and other such factors well known in the medical arts. These factors are discussed in Goodman and Gilman's "The Pharmacological Basis of Therapeutics", Tenth Edition, A. Gilman, J. Hardman and L. Limbird, eds., McGraw-Hill Press, 155-173, 2001, which is incorporated herein by reference.

Depending on the type of pharmaceutical composition, the pharmaceutically acceptable carrier may be chosen from any one or a combination of carriers known in the art. The choice of pharmaceutically acceptable carrier depends upon the pharmaceutical form and the desired method of administration to be used. For a pharmaceutical composition of the invention, that is one containing an olaparib hydroxybenzoic acid cocrystal of the invention, a carrier should be chosen that maintains the crystalline form. In other words, the carrier should not substantially alter the olaparib hydroxybenzoic acid cocrystal. Nor should the carrier be otherwise incompatible with the olaparib hydroxybenzoic acid cocrystal of the invention used, such as by producing any undesirable biological effect or otherwise interacting in a deleterious manner with any other component(s) of the pharmaceutical composition.

The pharmaceutical compositions of the invention may be prepared by methods known in the pharmaceutical formulation art, for example, see Remington's Pharmaceutical Sciences, 18th Ed., (Mack Publishing Company, Easton, Pa., 1990), which is incorporated herein by reference. In a solid dosage form, an olaparib hydroxybenzoic acid cocrystal of the invention may be admixed with at least one pharmaceutically acceptable excipient such as, for example, sodium citrate or dicalcium phosphate or (a) fillers or extenders, such as, for example, starches, lactose, sucrose, glucose, mannitol, and silicic acid, (b) binders, such as, for example, cellulose derivatives, starch, alginates, gelatin, polyvinylpyrrolidone, sucrose, and gum acacia, (c) humectants, such as, for example, glycerol, (d) disintegrating agents, such as, for example, agar-agar, calcium carbonate, potato or tapioca starch, alginic acid, croscarmellose sodium, complex silicates, and sodium carbonate, (e) solution retarders, such as, for example, paraffin, (f) absorption accelerators, such as, for example, quaternary ammonium compounds, (g) wetting agents, such as, for example, cetyl alcohol, and glycerol monostearate, magnesium stearate, and the like, (h) adsorbents, such as, for example, kaolin and bentonite, and (i) lubricants, such as, for example, talc, calcium stearate, magnesium stearate, solid polyethylene glycols, sodium lauryl sulfate, or mixtures thereof. In the case of capsules, tablets, and pills, the dosage forms may also comprise buffering agents. Pharmaceutically acceptable adjuvants known in the pharmaceutical formulation art may also be used in the pharmaceutical compositions of the invention. These include, but are not limited to, preserving, wetting, suspending, sweetening, flavoring, perfuming, emulsifying, and dispensing agents. Prevention of the action of microorganisms may be ensured by inclusion of various antibacterial and antifungal agents, for example, parabens, chlorobutanol, phenol, sorbic acid, and the like. It may also be desirable to include isotonic agents, for example, sugars, sodium chloride, and the like. If desired, a pharmaceutical composition of the invention may also contain minor amounts of auxiliary substances such as wetting or emulsifying agents, pH buffering agents, antioxidants, and the like, such as, for example, citric acid, sorbitan monolaurate, triethanolamine oleate, butylated hydroxytoluene, etc.

Solid dosage forms as described above may be prepared with coatings and shells, such as enteric coatings and others, as is known in the pharmaceutical art. They may contain pacifying agents and can also be of such composition that they release the active compound or compounds in a certain part of the intestinal tract in a delayed manner. Non-limiting examples of embedded compositions that may be used are polymeric substances and waxes. The active compounds may also be in microencapsulated form, such as pellets, if appropriate, with one or more of the above-mentioned excipients.

Suspensions, in addition to the active compounds, may contain suspending agents, such as, for example, ethoxylated isostearyl alcohols, polyoxyethylene sorbitol and sorbitan esters, microcrystalline cellulose, aluminum metahydroxide, bentonite, agar-agar and tragacanth, or mixtures of these substances, and the like. Liquid dosage forms may be aqueous, may contain a pharmaceutically acceptable solvent as well as traditional liquid dosage form excipients known in the art which include, but are not limited to, buffering agents, flavorants, sweetening agents, preservatives, and stabilizing agents.

Compositions for rectal administrations are, for example, suppositories that may be prepared by mixing an olaparib hydroxybenzoic acid cocrystal of the invention with, for example, suitable non-irritating excipients or carriers such as cocoa butter, polyethyleneglycol, or a suppository wax, which may be solid at ordinary temperatures but may be liquid at body temperature and, therefore, melt while in a suitable body cavity and release the active component therein.

Compositions suitable for topical administration include liquid or semi-liquid preparations such as liniments, lotions, gels, applicants, oil-in-water or water-in-oil emulsions such as creams, ointments, pastes, or foams; or solutions or suspensions such as drops, as is known in the art. Compositions of the invention may be intended for topical administration, in which case the carrier may suitably comprise a solution, emulsion, ointment, or gel base. The carrier or base, for example, may comprise one or more of the following: petrolatum, lanolin, polyethylene glycols, bee wax, mineral oil, diluents such as water and alcohol, and emulsifiers and stabilizers. Thickening agents may be present in a pharmaceutical composition for topical administration. If intended for transdermal administration, the composition may include a transdermal patch or iontophoresis device.

Topical formulations may contain a concentration of the compound of the invention from about 0.1 to about 10% w/v (weight per unit volume).

In addition to the topical method of administration described above, there are various methods of administering the olaparib hydroxybenzoic acid cocrystal of the invention topically to the lung. One such means could involve a dry powder inhaler formulation of particles that are of a size suitable for inhalation, typically <10 μm (i.e., in the respirable range) comprised of an olaparib hydroxybenzoic acid cocrystal of the invention, which the patient being treated inhales. Dry powder inhaler presentations can be unit dose capsules or blisters, multi-unit dose presentations, or reservoir presentations. The presentation could comprise the drug alone or include pharmaceutically acceptable carrier materials, as bulking agents and to which olaparib hydroxybenzoic acid cocrystal of the invention particles can adhere to. The carrier particles may be of any acceptable pharmacologically inert material or combination of materials. For example, the carrier particles may be composed of one or more materials selected from sugar alcohols; polyols, for example sorbitol, mannitol, or xylitol, and crystalline sugars, including monosaccharides and disaccharides; inorganic salts such as sodium chloride and calcium carbonate; organic salts such as sodium lactate; and other organic compounds such as urea, polysaccharides, for example cyclodextrins and dextrins. The carrier particles may be a crystalline sugar, for example, a monosaccharide such as glucose or arabinose, or a disaccharide such as maltose, saccharose, dextrose or lactose. Another means of administering the olaparib hydroxybenzoic acid cocrystal of the invention topically to the lung is via a solution made from a cocrystal of the invention or suspension of the drug particles formulated in a suitable aqueous based vehicle acceptable for inhalation and delivered by a nebulizer or spray, such as generated from jet nebulizers, vibrating mesh nebulizers or ultrasonic nebulizers. The vehicle can contain excipients acceptable for inhalation such as mannitol, glycerol, buffering agents such as phosphate or citrate buffers, sodium chloride, surfactants, and stabilizers. The particles generated from the solution or suspension can be liquid or solid, with a particle size sufficiently small to pass through the mouth and larynx upon inhalation and enter the lungs. A further means of administering the olaparib hydroxybenzoic acid cocrystal of the invention topically to the lung is via a non-aqueous pressurised solution or suspension delivered via a metered dose inhaler. The olaparib hydroxybenzoic acid cocrystal of the invention could be in solution or suspension in the formulation that could comprise propellants, cosolvents, stabilizers, and other excipients known in the art for the formulation of these dosage forms.

In addition to the topical method of administration described above, there are various methods of administering an olaparib hydroxybenzoic acid cocrystal of the invention systemically by such methods. One such means would involve an aerosol suspension of respirable particles comprised of an olaparib hydroxybenzoic acid cocrystal of the invention, which the patient being treated inhales. An olaparib hydroxybenzoic acid cocrystal of the invention would be absorbed into the bloodstream via the lungs in a pharmaceutically effective amount. The respirable particles can be liquid or solid, with a particle size sufficiently small to pass through the mouth and larynx upon inhalation.

Because the crystalline form of an olaparib hydroxybenzoic acid cocrystal of the invention may be maintained during preparation, solid dosage forms are one embodiment of the pharmaceutical composition of the invention. Dosage forms for oral administration, which includes capsules, tablets, pills, powders, granules, and suspensions may be used. Dosage forms for pulmonary administration, which includes metered dose inhaler, dry powder inhaler, or nebulizer formulations may be used. In such solid dosage forms, the active compound may be mixed with at least one inert, pharmaceutically acceptable excipient (also known as a pharmaceutically acceptable carrier).

An olaparib hydroxybenzoic acid cocrystal of the invention may also be used to formulate liquid or injectable pharmaceutical compositions. Administration of an olaparib hydroxybenzoic acid cocrystal of the invention in pure form or in an appropriate pharmaceutical composition may be carried out via any of the accepted modes of administration or agents for serving similar utilities. Thus, administration may be, for example, via the following routes: oral, buccal, nasal, pulmonary, parenteral (intravenous, intramuscular, or subcutaneous), topical, transdermal, intravaginal, intravesical, systemic, ophthalmic or rectal, in the form of solid, semi-solid, lyophilized powder, or liquid dosage forms (a solution, emulsion or suspension made from the cocrystals of the invention), such as, for example, tablets, suppositories, pills, soft elastic and hard gelatin capsules, powders, solutions, suspensions, sprays or aerosols, or the like, such as, for example, in unit dosage forms or multi-unit dosage forms suitable for simple administration of precise dosages. One route of administration may be oral administration, using a convenient daily dosage regimen that can be adjusted according to the degree of severity of the condition to be treated.

The invention also relates to a method of preparing a liquid pharmaceutical composition comprising the step of dissolving an olaparib hydroxybenzoic acid cocrystal of the invention in a pharmaceutically acceptable solvent and to liquid pharmaceutical compositions prepared according to that method. As discussed above, liquid pharmaceutical compositions of the invention may be administered orally, parenterally, by inhalation, and intravenously.

EXAMPLES

The following analytical methods were used to characterize the olaparib hydroxybenzoic acid cocrystals of the invention:

Bruker D8 X-Ray Powder Diffraction (XRPD) Characterization: X-ray powder diffraction patterns for the samples were acquired on a Bruker D8 diffractometer using Cu Kα radiation (40 kV, 40 mA) and a θ-2θ goniometer fitted with a Ge monochromator. The incident beam passes through a 2.0 mm divergence slit followed by a 0.2 mm anti-scatter slit and knife edge. The diffracted beam passes through an 8.0 mm receiving slit with 2.5° Soller slits followed by the Lynxeye Detector. The software used for data collection and analysis was Diffrac Plus XRD Commander and Diffrac Plus EVA respectively. Samples were run under ambient conditions over an angular range of 2° to 42° 2θ (using a step size of 0.05° 2θ and a step time of 0.5 seconds) as flat plate specimens using powder as received. The sample was prepared on a polished, zero-background (510) silicon wafer by gently pressing onto the flat surface or packed into a cut cavity. The sample was rotated in its own plane. Small D8 disc recess holders were used to prepare samples.

Bruker D2 X-Ray Powder Diffraction Characterisation: X-ray powder diffraction patterns for the samples were acquired on a Bruker 2nd Gen D2-Phaser diffractometer using CuKα radiation (30V, 10 mA), θ-2θ goniometer, V4 receiving slits, a Ge monochromator, and a Lynxeye detector. The instrument is performance checked using a certified Corundum standard (NIST 1976). The data were collected at ambient temperature over an angular range of 2° to 35° 2θ (using a step size of 0.05° 2θ and a step time of 2.0 seconds) or an angular range of 2° to 42° 2θ (using a step size of 0.025° 2θ and a step time of 5.0 seconds). Samples run under ambient conditions were prepared as flat plate specimens using powder as received without grinding. Approximately 20 mg of the sample was gently packed into sample holder and all samples were analysed using Diffrac Plus EVA v4.2.0.14

Differential Scanning calorimetry (DSC)—TA Q2000: DSC data were collected on a TA Instruments Q2000 equipped with a 50-position auto-sampler. Typically, 0.5-3 mg of each sample, in a pin-holed aluminum pan, was heated at 10° C./min from 25° C. to 300° C. A purge of dry nitrogen at 50 ml/min was maintained over the sample. The instrument control software was Advantage for Q Series and Thermal Advantage and the data were analyzed using Universal Analysis or TRIOS Differential Scanning calorimetry (DSC)—Pyris 4000: DSC data were collected on a PerkinElmer Pyris 4000 DSC equipped with a 45-position sample holder. The instrument was verified for energy and temperature calibration using certified indium. A predefined amount of the sample, 0.5-3.0 mg, was placed in a pin holed aluminium pan and heated at 20° C.min$^{-1}$ from 30 to 350° C. A purge of dry nitrogen at 60 ml.min$^{-1}$ was maintained over the sample. The instrument control, data acquisition, and analysis were performed with Pyris Software v9.0.1.0203.

Thermo-Gravimetric Analysis (TGA)—TA Q500:TGA data were collected on a TA Instruments Q500 TGA, equipped with a 16 position autosampler. Typically, 5-10 mg of each sample was loaded onto a pre-tared aluminium DSC pan and heated at 10° C./min from ambient temperature to 350° C. A nitrogen purge at 60 ml/min was maintained over the sample. The instrument control software was Advantage for Q Series and Thermal Advantage and the data were analysed using Universal Analysis or TRIOS.

Thermo-Gravimetric Analysis (TGA)—Perkin Elmer 4000: TGA data was collected on a Perkin Elmer TGA 4000 system. The calibration for the energy and temperature was carried out using certified indium. Typically 2-5 mg of each sample was heated at 20° C./min in an atmosphere of Nitrogen maintained at 20 ml/min. The instrument control software was Perkin Elmer Pryis Thermal Analysis v11.1.1.0492. All data analysis was performed using Pyris Thermal Analysis software v13.3.1.0014.

Solution Proton Nuclear Magnetic Resonance ($^1$H-NMR): $^1$H-NMR spectra were collected using a JEOL EX 270 MHz spectrometer equipped with an auto-sampler. The samples were dissolved in d6-DMSO for analysis. The data was acquired using Delta NMR Processing and Control Software version 4.3.

Scanning Electron Microscopy (SEM): Data were collected on a Phenom Pro Scanning Electron Microscope. A small quantity of sample was mounted onto an aluminum stub using conducting double-sided adhesive tape. A thin layer of gold was applied using a sputter coater (20 mA, 120 s).

Gravimetric Vapour Sorption (GVS): Sorption isotherms were obtained using a SMS DVS Intrinsic moisture sorption analyzer, controlled by DVS Intrinsic Control software. The sample temperature was maintained at 25° C. by the instrument controls. The humidity was controlled by mixing streams of dry and wet nitrogen, with a total flow rate of 200 ml/min. The relative humidity was measured by a calibrated Rotronic probe (dynamic range of 1.0-100% RH), located near the sample. The weight change, (mass relaxation) of the sample as a function of % RH was constantly monitored by a microbalance (accuracy ±0.005 mg).

Typically, 5-30 mg of sample was placed in a tared mesh stainless steel basket under ambient conditions. The sample was loaded and unloaded at 40% RH and 25° C. (typical room conditions). A moisture sorption isotherm was performed as outlined in Table 1 (2 scans per complete cycle). The standard isotherm was performed at 25° C. at 10% RH intervals over a 0-90% RH range. Typically, a double cycle (4 scans) was carried out. Data analysis was carried out within Microsoft Excel using the DVS Analysis Suite. The sample was recovered after completion of the isotherm and re-analyzed by XRPD.

TABLE 1

| Method for SMS DVS Intrinsic experiments | |
|---|---|
| Parameter | Value |
| Adsorption-Scan 1 | 40-90 |
| Desorption, Adsorption-Scan 2 | 90-0, 0-40 |
| Intervals (% RH) | 10 |
| Number of Scans | 4 |
| Flow rate (ml/min) | 200 |
| Temperature (° C.) | 25 |
| Stability (° C./min) | 0.2 |
| Sorption Time (hours) | 6 hour time out |
| Number of cycles | 2 |

Karl Fischer Titration: The water content of each sample was measured on a Metrohm 874 Oven Sample Processor at 150° C. with 851 Titrano Coulometer using Hydranal Coulomat AG oven reagent and nitrogen purge. Weighed solid samples were introduced into a sealed sample vial. Approximately 10 mg of sample was used per titration and duplicate determinations were made. An average of these results is presented unless otherwise stated. Data collection and analysis were performed using Tiamo software.

Chemical Purity Determination by HPLC: Purity analysis was performed on an Agilent HP1100/Infinity II 1260 series system equipped with a diode array detector and using Open LAB software. The full method details are provided in Table 2:

TABLE 2

| HPLC method for chemical purity determinations | | | |
|---|---|---|---|
| Parameter | Value | | |
| Type of method | Reverse phase with gradient elution | | |
| Sample Preparation | 0.2-0.5 mg/ml in acetonitrile:water 1:1 | | |
| Column | Supelco Ascentis Express C18 2.7 µm 100 × 4.6 mm | | |
| Column Temperature (° C.) | 25 | | |
| Injection (µl) | 5 | | |
| Detection: Wavelength, Bandwidth (nm) | 255, 90 | | |
| Flow Rate (ml/min) | 2 | | |
| Phase A | 0.1% TFA in water | | |
| Phase B | 0.085% TFA in acetonitrile | | |
| Timetable | Time (min) | % Phase A | % Phase B |
| | 0 | 95 | 5 |
| | 6 | 5 | 95 |
| | 6.2 | 95 | 5 |
| | 8 | 95 | 5 |

Fourier Transform Infrared: Data were collected on a Perkin-Elmer Spectrum One fitted with a universal Attenuated Total Reflectance (ATR) sampling accessory from 4000-650 $cm^{-1}$ over 16 scans. The data were collected using Spectrum software and processed using ACD Spectrus Processor.

Example 1

1:1 Olaparib Gentisic Acid Cocrystal 1.1 Preparation of the 1:1 Olaparib Gentisic Acid Cocrystal The batch of 1:1 olaparib gentisic acid cocrystal used for characterization was prepared as follows:

Olaparib (500 mg, 1.15 mmol) and gentisic acid (178 mg, 1.15 mmol) were milled together with acetonitrile (200 μL) for 6×20 minutes at 30 Hz in a Retsch MM400 ball mill. The product was dried in-vacuo at 40° C. for 2 hours.

1.2 XRPD Characterization of the 1:1 Olaparib Gentisic Acid Cocrystal

Figure 1:
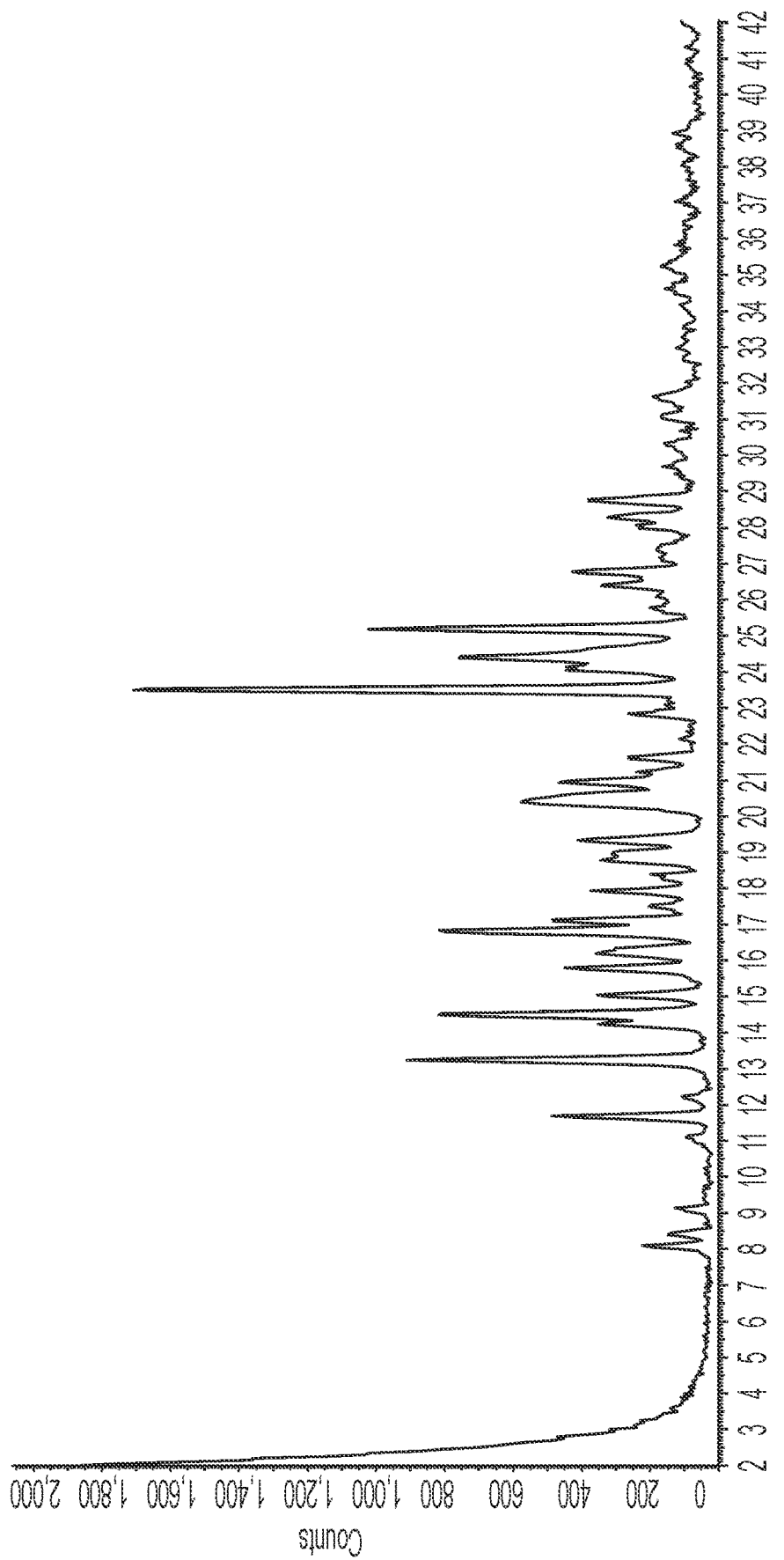
FIG. 1 shows an XRPD pattern of the 1:1 olaparib gentisic acid cocrystal.

The D8 XRPD pattern of the 1:1 olaparib gentisic acid cocrystal is shown in FIG. 1. Table 3 lists the angles, °2θ±0.2°2θ, and d value of the peaks identified in the XRPD pattern of FIG. 1. The entire list of peaks or corresponding d values, or a subset thereof, may be sufficient to characterize the cocrystal, as well as by an XRPD pattern substantially similar to FIG. 1. For example, the cocrystal may be characterized by at least two, at least three, at least four, or all of the peaks selected from the peaks at 11.7, 13.2, 15.0, 23.5, and 25.2°2θ±0.2°2θ.

TABLE 3

| Angle °2θ ± 0.2 °2θ | d value Angstrom | Intensity % |
|---|---|---|
| 8.1 | 10.93 | 10% |
| 8.4 | 10.51 | 6% |
| 9.1 | 9.70 | 4% |
| 11.1 | 7.96 | 7% |
| 11.7 | 7.57 | 24% |
| 13.2 | 6.68 | 50% |
| 14.2 | 6.22 | 25% |
| 14.5 | 6.10 | 43% |
| 15.0 | 5.89 | 16% |
| 15.8 | 5.61 | 22% |
| 16.2 | 5.46 | 15% |
| 16.8 | 5.27 | 42% |
| 17.1 | 5.18 | 39% |
| 17.5 | 5.07 | 7% |
| 17.9 | 4.94 | 17% |
| 18.3 | 4.85 | 8% |
| 18.4 | 4.82 | 10% |
| 18.8 | 4.72 | 25% |
| 19.0 | 4.68 | 14% |
| 19.3 | 4.59 | 21% |
| 20.4 | 4.35 | 29% |
| 21.0 | 4.24 | 23% |
| 21.2 | 4.18 | 15% |
| 21.6 | 4.11 | 11% |
| 22.8 | 3.89 | 11% |
| 23.5 | 3.78 | 100% |
| 24.0 | 3.70 | 23% |
| 24.1 | 3.68 | 31% |
| 24.4 | 3.65 | 40% |
| 25.2 | 3.53 | 57% |
| 25.8 | 3.45 | 5% |
| 26.4 | 3.37 | 14% |
| 26.8 | 3.33 | 19% |
| 28.1 | 3.18 | 10% |
| 28.3 | 3.15 | 14% |
| 28.7 | 3.10 | 18% |
| 31.1 | 2.88 | 5% |

TABLE 3-continued

| Angle °2θ ± 0.2 °2θ | d value Angstrom | Intensity % |
|---|---|---|
| 31.6 | 2.83 | 6% |
| 35.3 | 2.54 | 5% |

1.3 DSC of the 1:1 Olaparib Gentisic Acid Cocrystal

Figure 2:
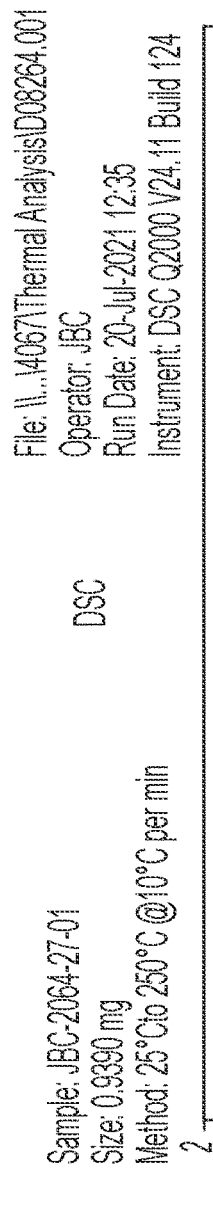
FIG. 2 shows a DSC trace for the 1:1 olaparib gentisic acid cocrystal.

The DSC trace of the 1:1 olaparib gentisic acid cocrystal as obtained on the TA Q2000 instrument, FIG. 2, shows a single endotherm with an onset temperature of 155.2° C. and a peak maximum of 158.0° C.

1.4 TGA of the 1:1 Olaparib Gentisic Acid Cocrystal

Figure 3:
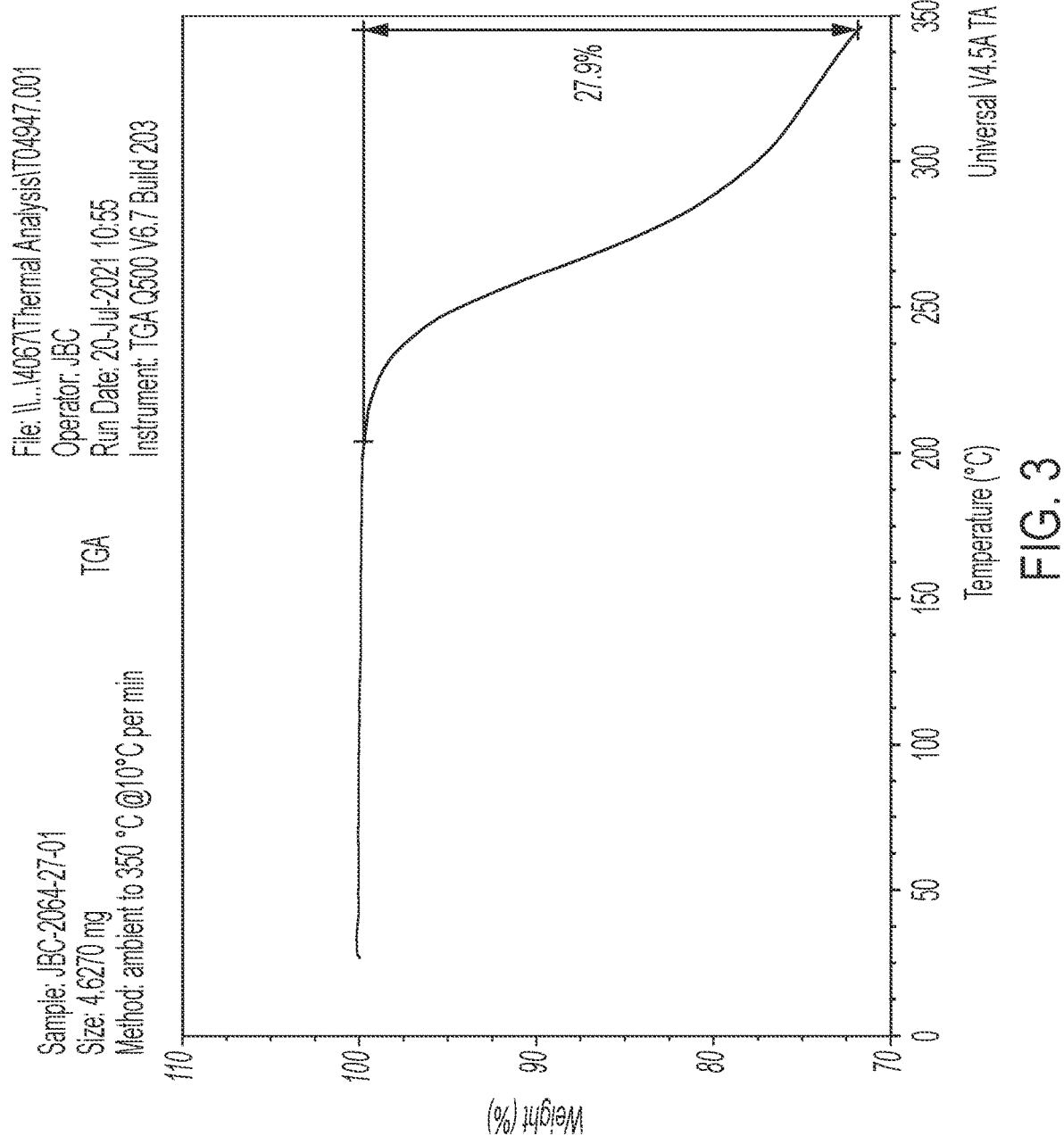
FIG. 3 shows a TGA trace for the 1:1 olaparib gentisic acid cocrystal.

In the TGA trace of the 1:1 olaparib gentisic acid cocrystal as obtained on the TA Q500 instrument, FIG. 3, there is no significant weight loss until after 200° C., at which point a 26% weight loss is observed, which corresponds to the loss of 1 mole of gentisic acid. This shows that the cocrystal has 1:1 olaparib:gentisic acid stoichiometry and that the cocrystal is anhydrous.

1.5 Infrared Spectrum of the 1:1 Olaparib Gentisic Acid Cocrystal

Figure 4:
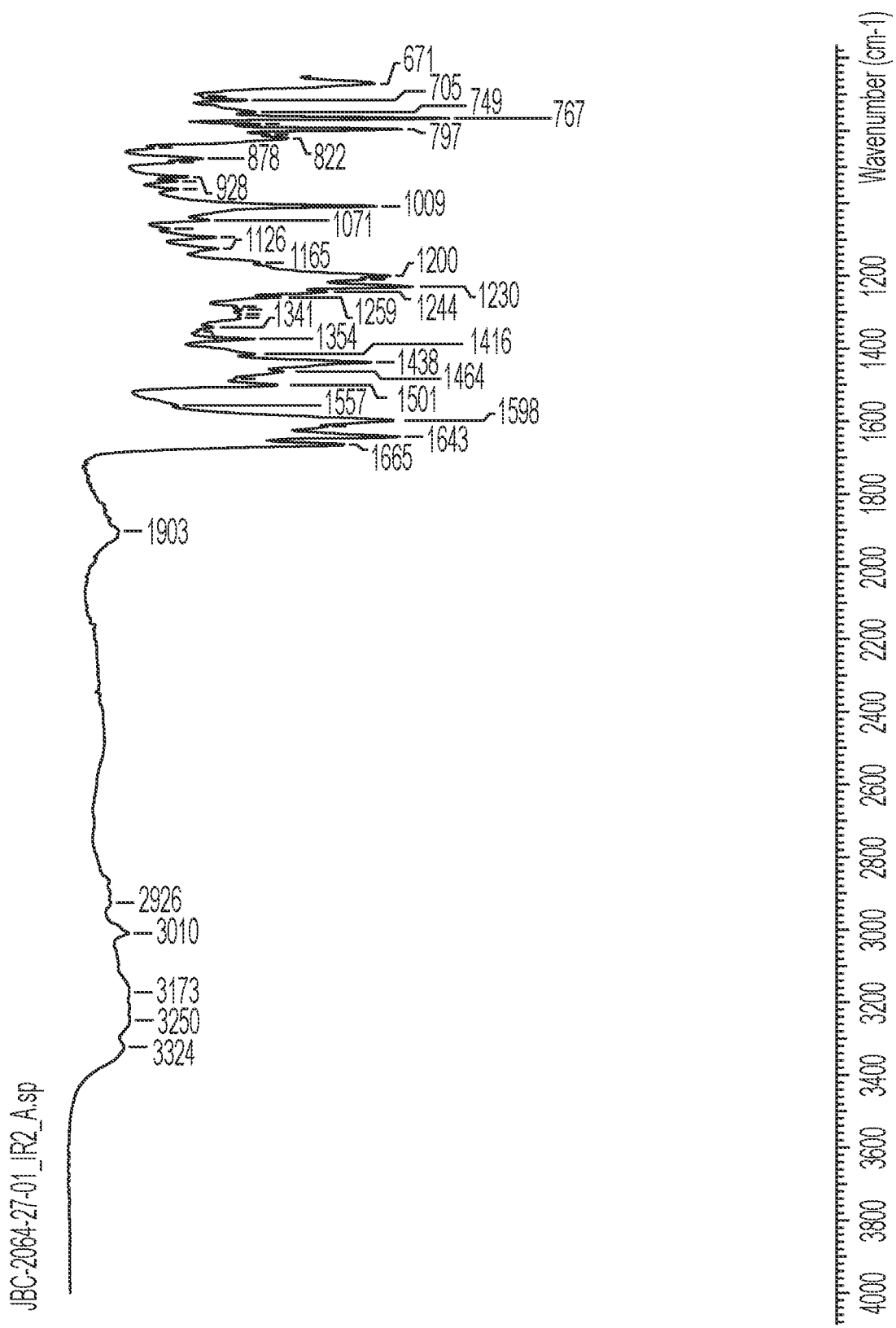
FIG. 4 shows an Infrared spectrum for the 1:1 olaparib gentisic acid cocrystal.

The infrared spectrum of the 1:1 olaparib gentisic acid cocrystal is shown in FIG. 4. The significant peaks identified in the infrared spectrum of FIG. 4 are 3010, 1903, 1665, 1643, 1598, 1557, 1501, 1464, 1438, 1354, 1341, 1259, 1244, 1230, 1200, 1165, 1126, 1021, 1009, 928, 878, 822, 797, 767, 749, 705, and 671 $cm^{-1}$±1 $cm^{-1}$. The entire list of peaks, or a subset thereof, may be sufficient to characterize the cocrystal, as well as by an infrared pattern substantially similar to FIG. 4.

Example 2

2:1 Olaparib Gentisic Acid Cocrystal 2.1 Preparation of the 2:1 Olaparib Gentisic Acid Cocrystal The batch of 2:1 olaparib gentisic acid cocrystal used for characterization was prepared as follows:

Olaparib (500 mg, 1.15 mmol) and gentisic acid (88 mg, 0.57 mmol) were milled together with water (200 μL) for 3×20 minutes at 30 Hz in a Retsch MM400 ball mill. The product was dried in-vacuo at 40° C. for 2 hours.

2.2 XRPD Characterization of the 2:1 Olaparib Gentisic Acid Cocrystal

Figure 5:
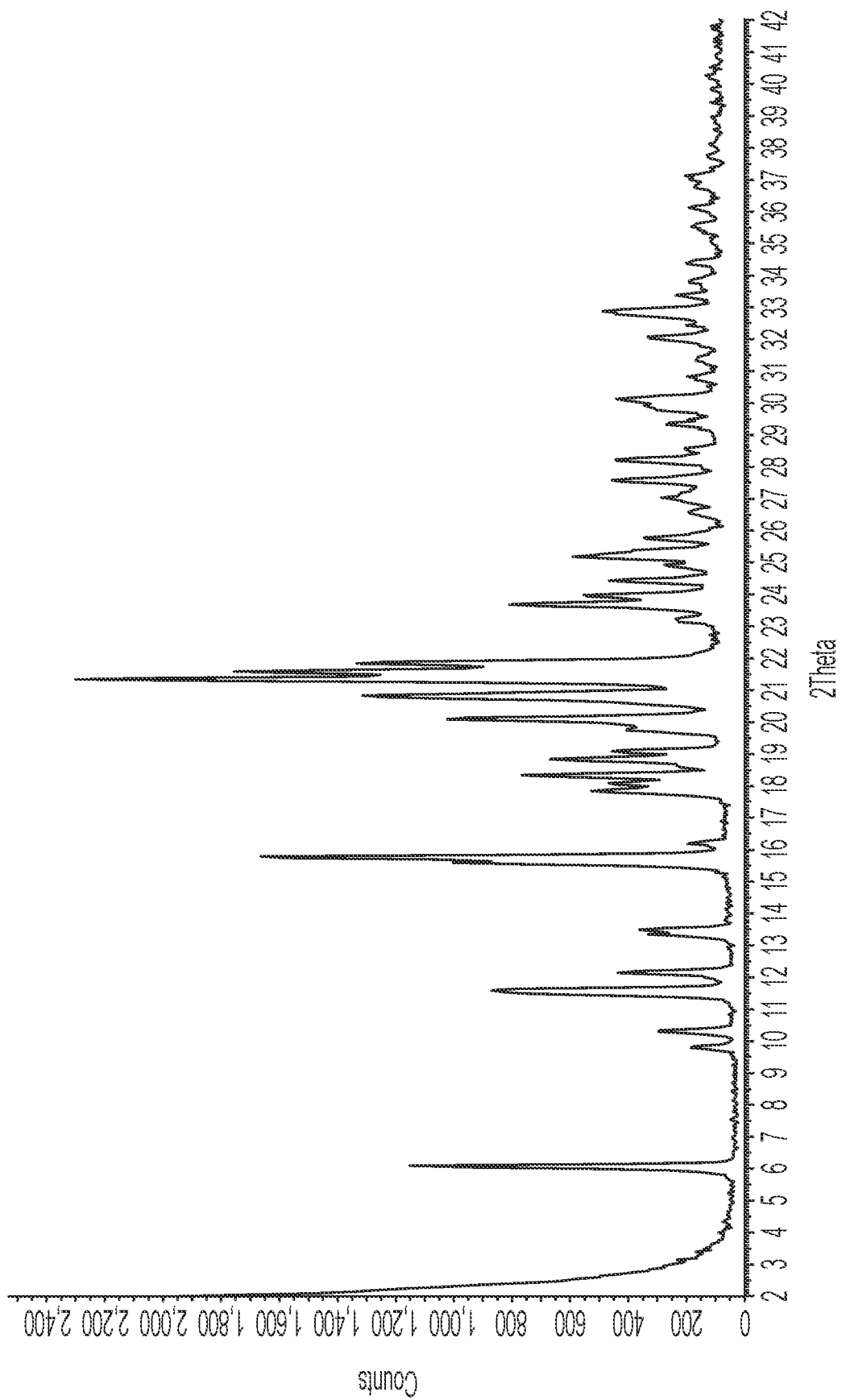
FIG. 5 shows an XRPD pattern of the 2:1 olaparib gentisic acid cocrystal.

The D8 XRPD pattern of the 2:1 olaparib gentisic acid cocrystal is shown in FIG. 5. Table 4 lists the angles, °2θ±0.2°2θ, and d value of the peaks identified in the XRPD pattern of FIG. 5. The entire list of peaks or corresponding d values, or a subset thereof, may be sufficient to characterize the cocrystal, as well as by an XRPD pattern substantially similar to FIG. 5. For example, the cocrystal may be characterized by at least two, at least three, at least four, or all of the peaks selected from the peaks at 6.1, 10.3, 11.6, 12.2, and 20.8°2θ±0.2°2θ.

TABLE 4

| Angle °2θ ± 0.2 °2θ | d value Angstrom | Intensity % |
|---|---|---|
| 6.1 | 14.53 | 40% |
| 9.8 | 9.02 | 6% |
| 10.3 | 8.58 | 11% |
| 11.6 | 7.65 | 33% |
| 12.2 | 7.28 | 16% |

TABLE 4-continued

| Angle °2θ ± 0.2 °2θ | d value Angstrom | Intensity % |
|---|---|---|
| 13.3 | 6.64 | 17% |
| 13.5 | 6.57 | 13% |
| 15.6 | 5.68 | 67% |
| 15.8 | 5.62 | 70% |
| 16.2 | 5.47 | 6% |
| 17.8 | 4.97 | 19% |
| 18.1 | 4.90 | 17% |
| 18.3 | 4.84 | 30% |
| 18.8 | 4.71 | 26% |
| 19.1 | 4.65 | 16% |
| 19.8 | 4.48 | 13% |
| 20.1 | 4.42 | 42% |
| 20.8 | 4.26 | 54% |
| 21.3 | 4.16 | 100% |
| 21.6 | 4.12 | 75% |
| 21.8 | 4.07 | 60% |
| 23.2 | 3.83 | 6% |
| 23.7 | 3.75 | 32% |
| 24.0 | 3.71 | 20% |
| 24.4 | 3.64 | 17% |
| 24.9 | 3.57 | 8% |
| 25.2 | 3.53 | 20% |
| 25.8 | 3.45 | 11% |
| 27.0 | 3.29 | 8% |
| 27.6 | 3.23 | 16% |
| 28.2 | 3.16 | 15% |
| 29.4 | 3.04 | 7% |
| 29.9 | 2.98 | 10% |
| 30.1 | 2.97 | 15% |
| 32.1 | 2.79 | 10% |
| 32.9 | 2.72 | 16% |
| 33.4 | 2.68 | 6% |

2.3 DSC of the 2:1 Olaparib Gentisic Acid Cocrystal

Figure 6:
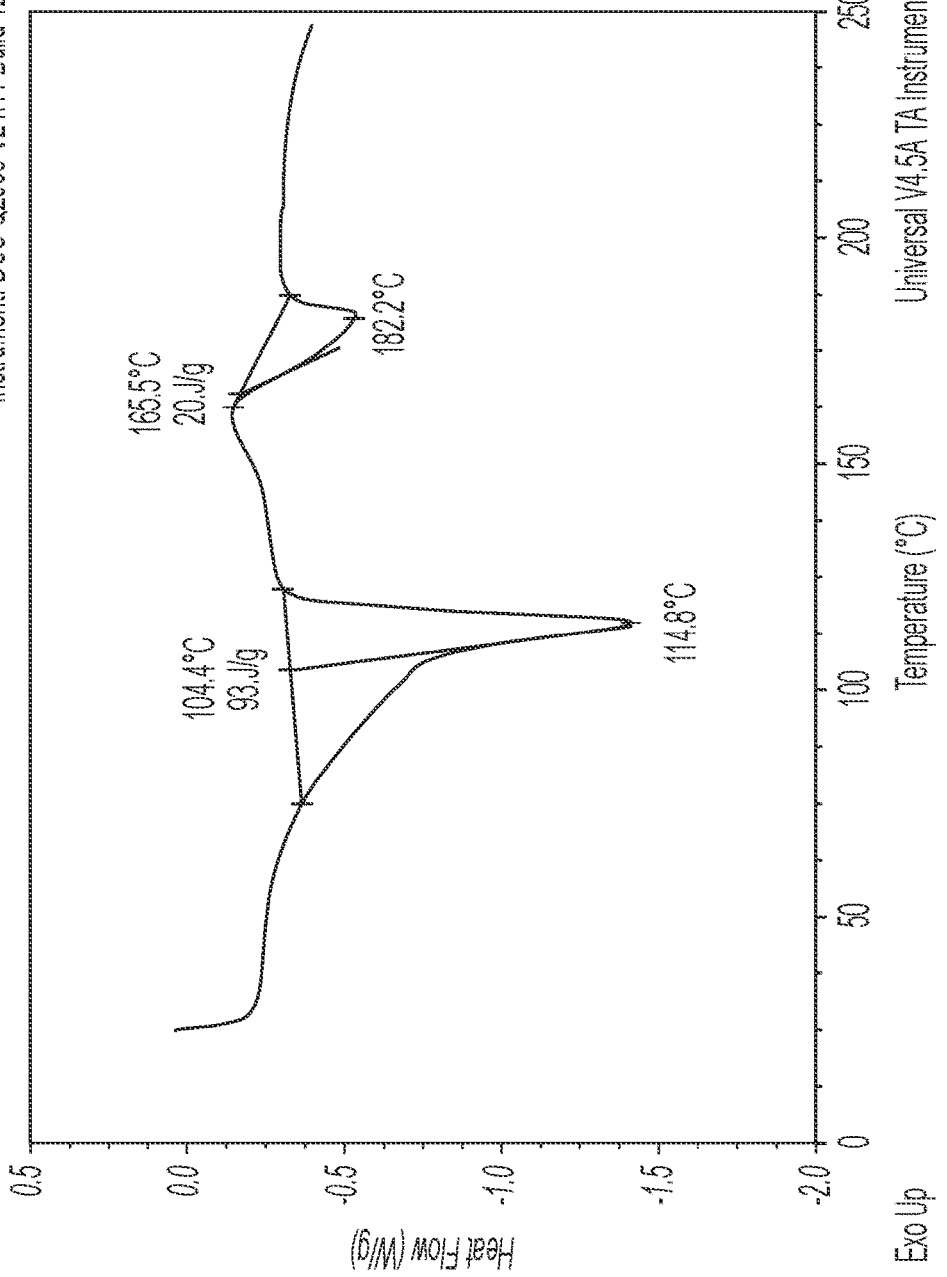
FIG. 6 shows a DSC trace for the 2:1 olaparib gentisic acid cocrystal.

The DSC trace of the 2:1 olaparib gentisic acid cocrystal as obtained on the TA Q2000 instrument, FIG. 6, shows an endotherm with an onset temperature of 104.4° C. and a peak maximum of 114.8° C. followed by a second broad endotherm with an onset temperature of 165.5° C. and a peak maximum of 182.2° C.

2.4 TGA of the 2:1 Olaparib Gentisic Acid Cocrystal

Figure 7:
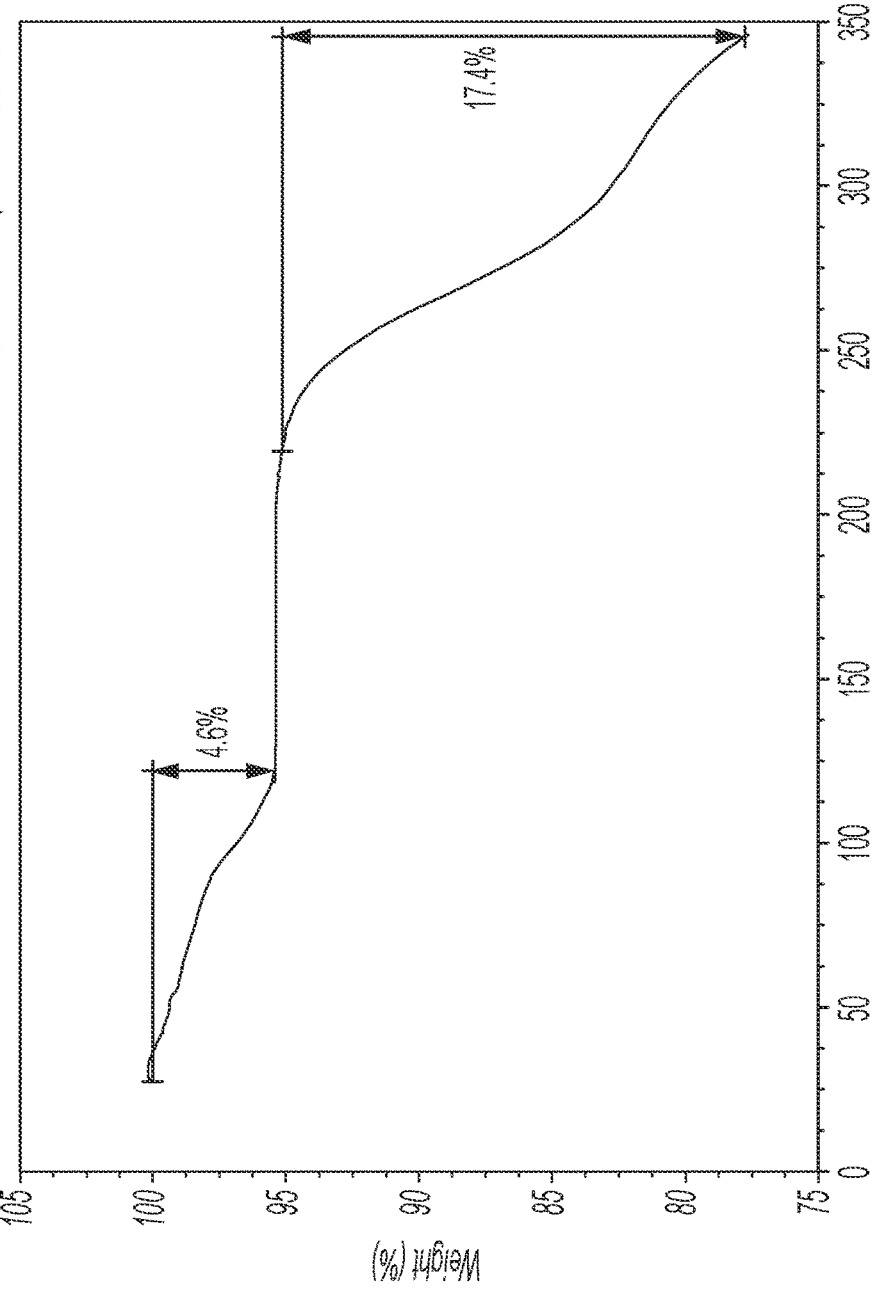
FIG. 7 shows a TGA trace for the 2:1 olaparib gentisic acid cocrystal.

In the TGA trace of the 2:1 olaparib gentisic acid cocrystal as obtained on the TA Q500 instrument, FIG. 7, there is a weight loss of 4.6% between room temperature and 120° C.

2.5 Infrared Spectrum of the 2:1 Olaparib Gentisic Acid Cocrystal

Figure 8:
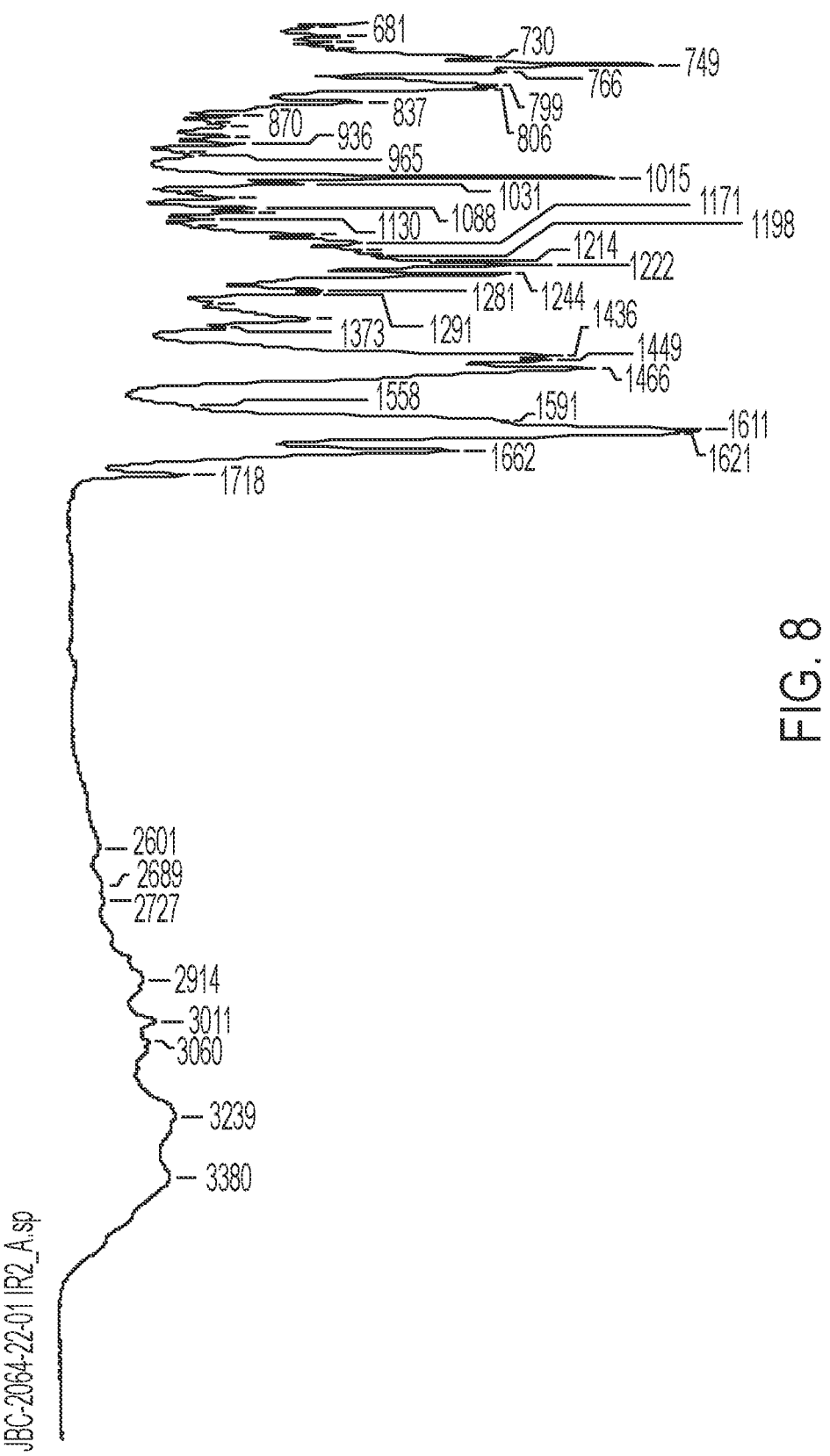
FIG. 8 shows an Infrared spectrum for the 2:1 olaparib gentisic acid cocrystal.

The infrared spectrum of the 2:1 olaparib gentisic acid cocrystal is shown in FIG. 8. The significant peaks identified in the infrared spectrum of FIG. 8 are 3380, 3239, 3011, 1718, 1662, 1611, 1591, 1266, 1449, 1436, 1373, 1291, 1281, 1244, 1222, 1214, 1198, 1171, 1088, 1031, 1015, 936, 870, 837, 806, 799, 766, 749, 730, and 681 cm$^{-1}$±1 cm$^{-1}$. The entire list of peaks, or a subset thereof, may be sufficient to characterize the cocrystal, as well as by an infrared pattern substantially similar to FIG. 8. For example, the cocrystal may be characterized by at least two, at least three, at least four, or all of the peaks selected from the peaks at 1014, 1222, 1243, 1435, and 1590 cm$^{-1}$±1 cm$^{-1}$.

Figure 9:
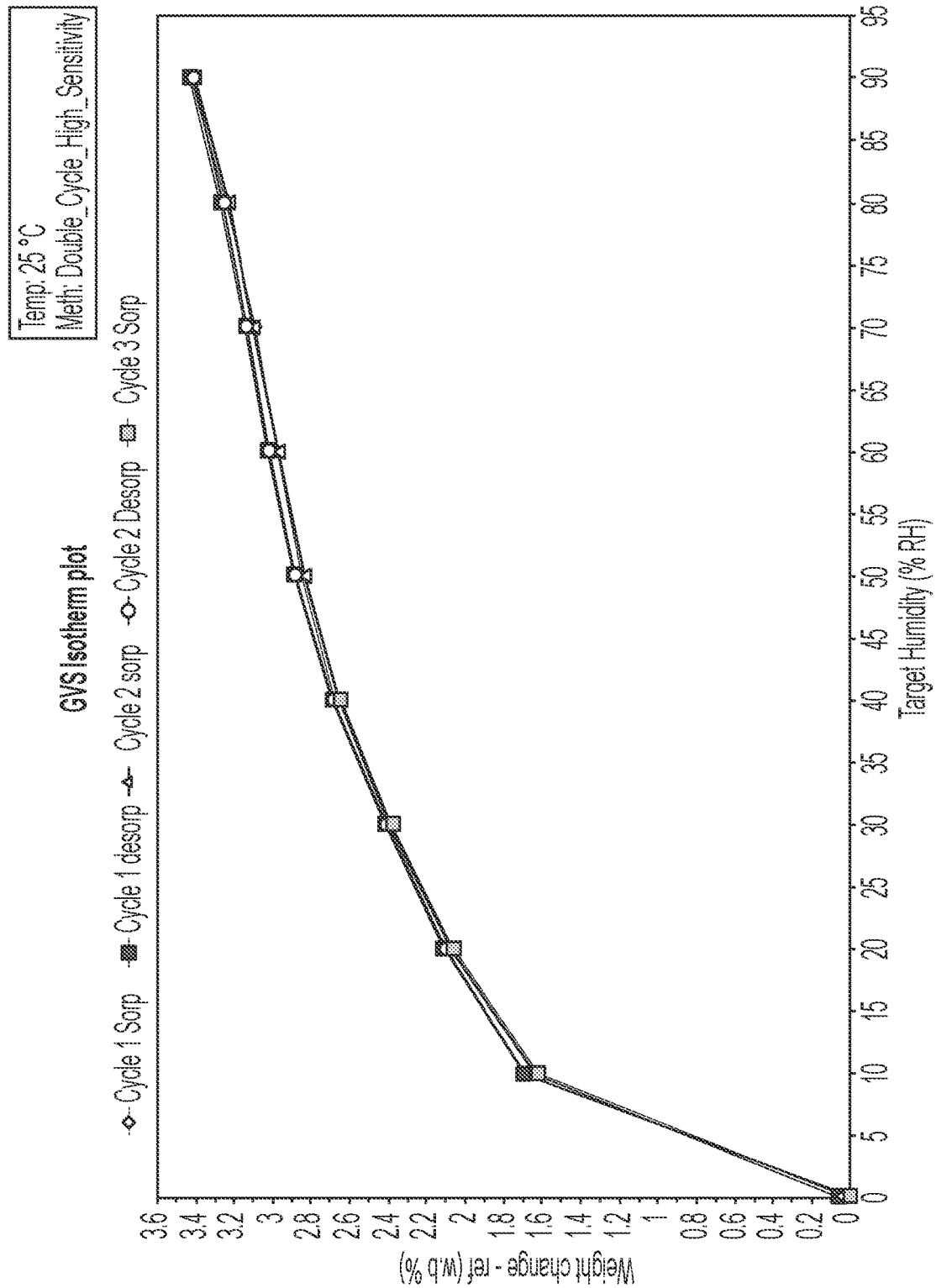
FIG. 9 shows a GVS isotherm graph for the 2:1 olaparib gentisic acid cocrystal.

2.6 Gravimetric Vapour Sorption (GVS) Analysis of the 2:1 Olaparib Gentisic Acid Cocrystal The moisture sorption isotherm graph obtained for the 2:1 olaparib gentisic acid cocrystal is shown in FIG. 9. The cocrystal was found to reversibly absorb 3.4% w/w across the 0-90% relative humidity range at 25° C. under nitrogen (1.6% w/w was reversibly absorbed between 0 and 5% RH). XRPD analysis of the sample post GVS confirmed that the cocrystal structure was unchanged.

2.7 Karl Fischer Titration of the 2:1 Olaparib Gentisic Acid Cocrystal

Karl Fischer analysis of the 2:1 olaparib gentisic cocrystal indicated that the sample contained 5.1% water, which is equivalent to three moles of water.

Example 3

1:1 Olaparib 2,4-Dihydroxybenzoic Acid Cocrystal 3.1 Preparation of the 1:1 Olaparib 2,4-Dihydroxybenzoic Acid Cocrystal The batch of 1:1 olaparib 2,4-dihydroxybenzoic acid cocrystal used for characterization was prepared as follows:

Olaparib (400 mg, 0.92 mmol) and 2,4-dihydroxybenzoic acid (144 mg, 0.93 mmol) were milled together with acetonitrile (200 µl) for 6×20 minutes at 30 Hz in a Retsch M M400 ball mill. The product was dried in-vacuo at 40° C. for 2 hours.

Figure 10:
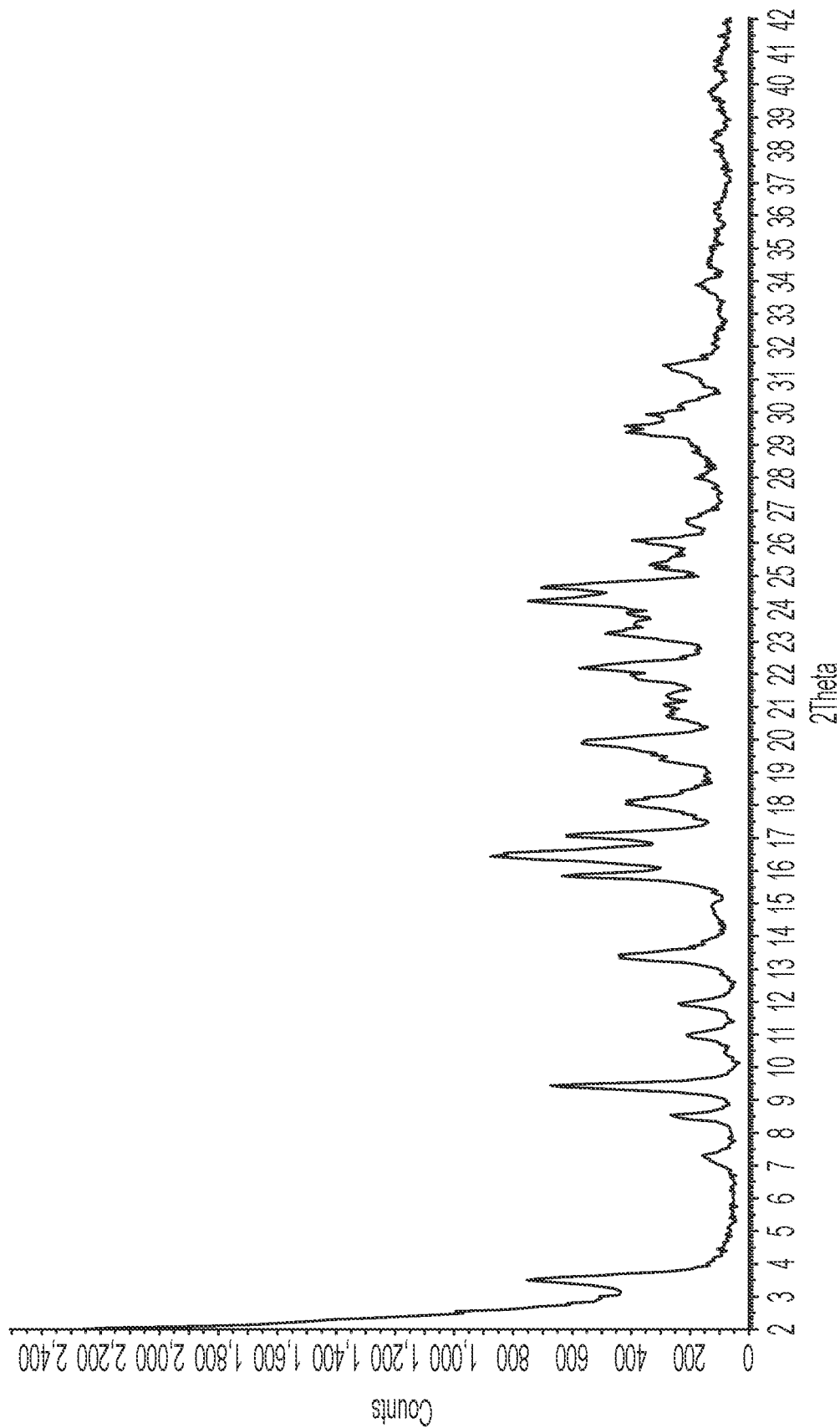
FIG. 10 shows an XRPD pattern of the 1:1 olaparib 2,4-dihydroxybenzoic acid cocrystal.

3.2 XRPD Characterization of the 1:1 Olaparib 2,4-Dihydroxybenzoic Acid Cocrystal The D8 XRPD pattern of the 1:1 olaparib 2,4-dihydroxybenzoic acid cocrystal is shown in FIG. 10. Table 5 lists the angles, °2θ±0.2°2θ, and d value of the peaks identified in the XRPD pattern of FIG. 10. The entire list of peaks or corresponding d values, or a subset thereof, may be sufficient to characterize the cocrystal, as well as by an XRPD pattern substantially similar to FIG. 10. For example, the cocrystal may be characterized by at least two, at least three, at least four, or all of the peaks selected from the peaks at 3.5, 8.5, 9.4, 11.9, and 16.5°2θ±0.2°2θ.

TABLE 5

| Angle °2θ ± 0.2 °2θ | d value Angstrom | Intensity % |
|---|---|---|
| 3.5 | 25.16 | 44% |
| 7.3 | 12.16 | 11% |
| 8.5 | 10.39 | 24% |
| 9.4 | 9.37 | 81% |
| 11.0 | 8.05 | 20% |
| 11.9 | 7.41 | 23% |
| 13.4 | 6.61 | 48% |
| 15.8 | 5.59 | 74% |
| 16.5 | 5.38 | 100% |
| 17.1 | 5.19 | 69% |
| 18.1 | 4.90 | 36% |
| 19.9 | 4.45 | 60% |
| 20.7 | 4.28 | 30% |
| 20.9 | 4.26 | 22% |
| 21.1 | 4.21 | 27% |
| 21.3 | 4.16 | 16% |
| 22.0 | 4.05 | 33% |
| 22.2 | 4.00 | 59% |
| 23.3 | 3.82 | 47% |
| 24.2 | 3.67 | 89% |
| 24.7 | 3.61 | 83% |
| 25.3 | 3.51 | 28% |
| 26.1 | 3.42 | 34% |
| 26.6 | 3.34 | 13% |
| 29.4 | 3.03 | 39% |
| 29.9 | 2.98 | 34% |
| 30.2 | 2.96 | 19% |
| 31.4 | 2.85 | 25% |

3.3 DSC of the 1:1 Olaparib 2,4-Dihydroxybenzoic Acid Cocrystal

Figure 11:
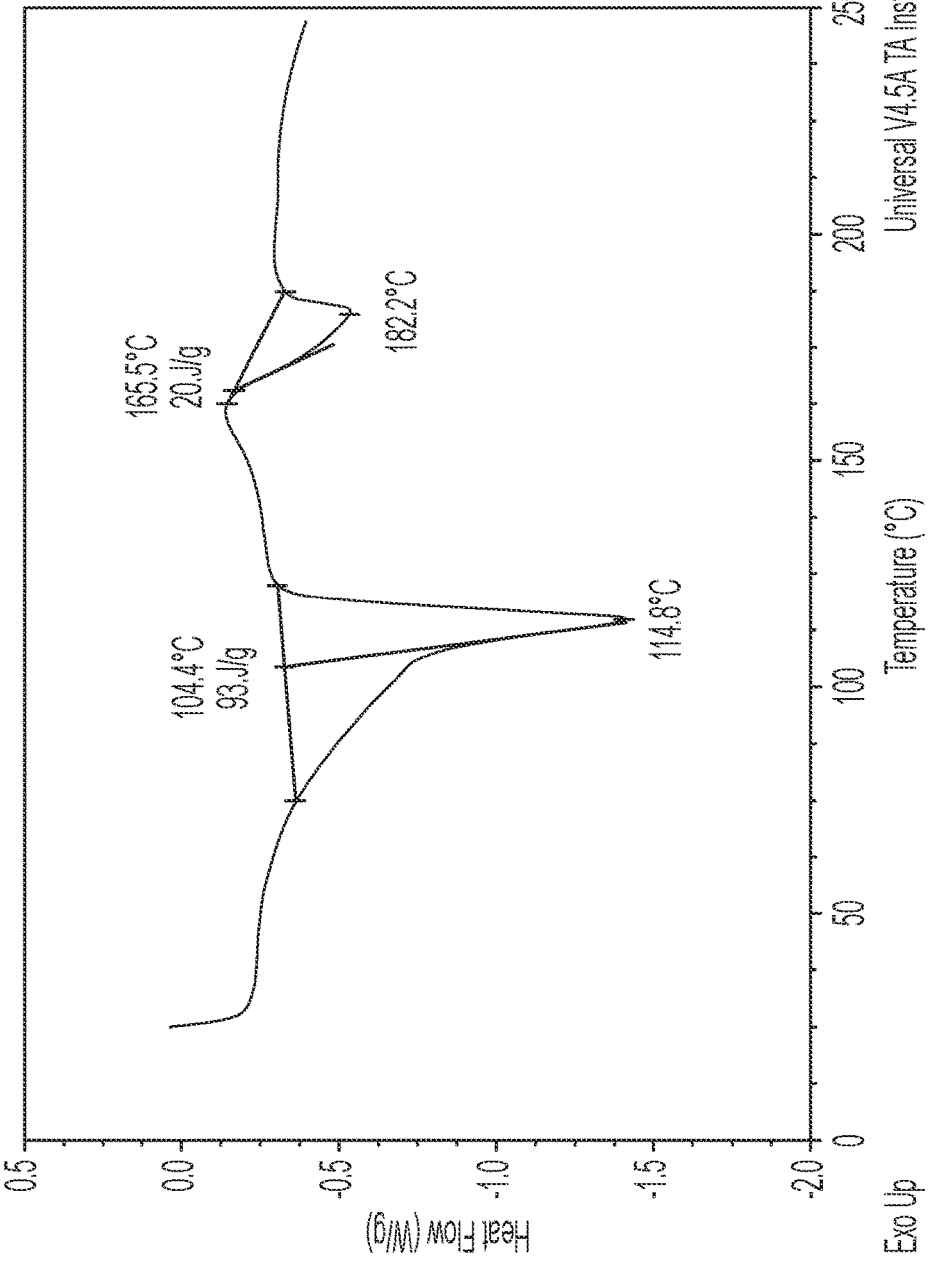
FIG. 11 shows a DSC trace for the 1:1 olaparib 2,4-dihydroxybenzoic acid cocrystal.

The DSC trace of the 1:1 olaparib 2,4-dihydroxybenzoic acid cocrystal as obtained on the TA Q2000 instrument, FIG. 11, shows an endotherm with an onset temperature of 132.1° C. and a peak maximum of 143.6° C. followed by a second broad endotherm with an onset temperature of 180.1° C. and a peak maximum of 203.1° C.

3.4 TGA of the 1:1 Olaparib 2,4-Dihydroxybenzoic Acid Cocrystal

Figure 12:
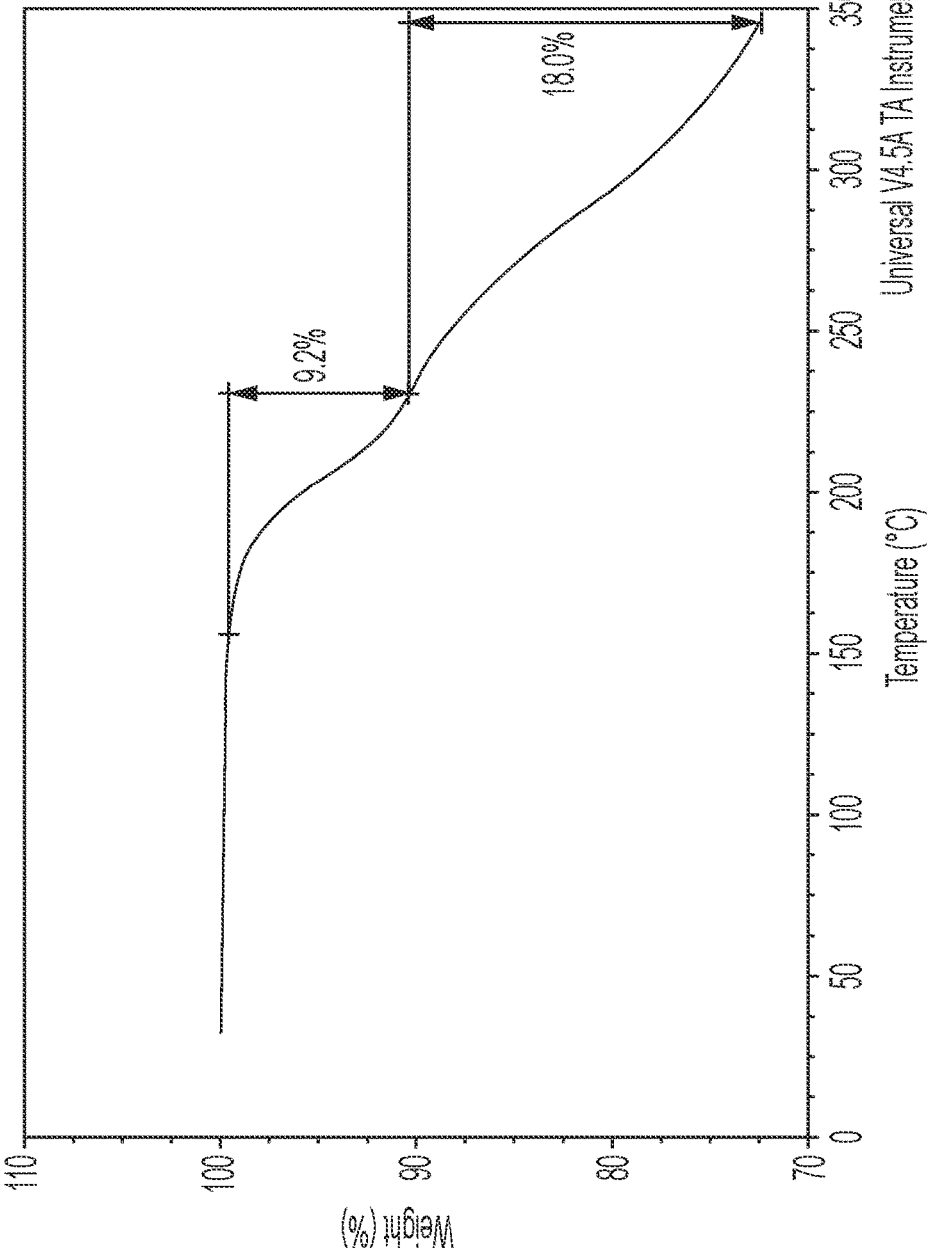
FIG. 12 shows a TGA trace for the 1:1 olaparib 2,4-dihydroxybenzoic acid cocrystal.

In the TGA trace of the 1:1 olaparib 2,4-dihydroxybenzoic acid cocrystal as obtained on the TA Q500 instrument, FIG. 12, there is no significant weight loss until after 150° C.

3.5 Infrared Spectrum of the 1:1 Olaparib 2,4-Dihydroxybenzoic Acid Cocrystal

Figure 13:
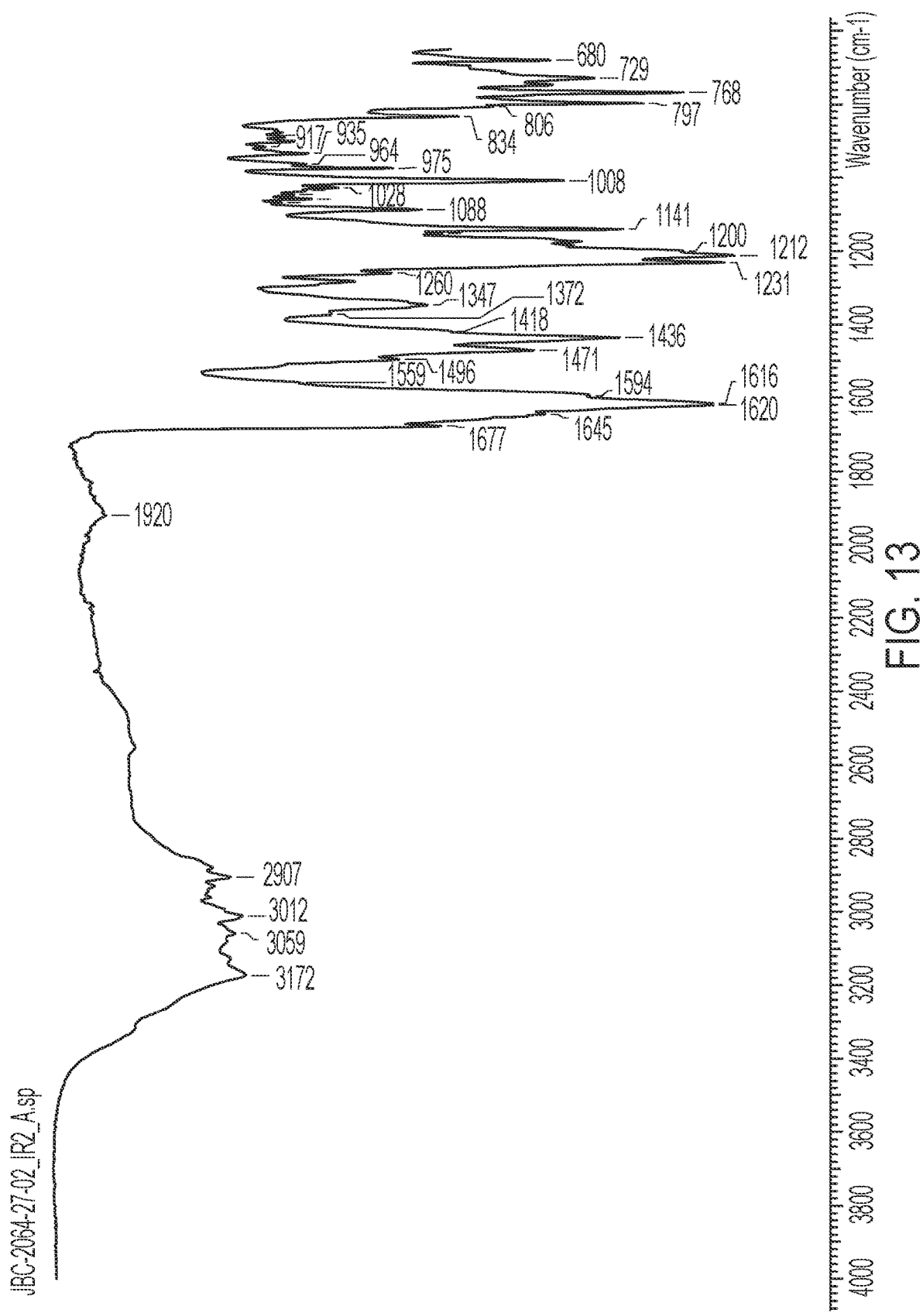
FIG. 13 shows an Infrared spectrum for the 1:1 olaparib 2,4-dihydroxybenzoic acid cocrystal.

The infrared spectrum of the 1:1 olaparib 2,4-dihydroxybenzoic acid cocrystal is shown in FIG. 13. The significant peaks identified in the infrared spectrum of FIG. 13 are 3172, 3012, 2907, 1677, 1645, 1620, 1594, 1599, 1496, 1471, 1436, 1347, 1260, 1321, 1212, 1200, 1141, 1088, 1028, 1008, 975, 964, 935, 834, 806, 797, 768, 729, and 680 $cm^{-1} \pm 1\ cm^{-1}$. The entire list of peaks, or a subset thereof, may be sufficient to characterize the cocrystal, as well as by an infrared pattern substantially similar to FIG. 13.

Example 4

2:1 Olaparib 2,4-Dihydroxybenzoic Acid Cocrystal 4.1 Preparation of the 2:1 Olaparib 2,4-Dihydroxybenzoic Acid Cocrystal The batch of 2:1 olaparib 2,4-dihydroxybenzoic acid cocrystal used for characterization was prepared as follows:

Olaparib (500 mg, 1.15 mmol) and 2,4-dihydroxybenzoic acid (90 mg, 0.58 mmol) were milled together with water (100 µL) and ethanol (100 µL) for 3×20 minutes at 30 Hz in a Retsch MM400 ball mill. The product was dried in-vacuo at 40° C. for 2 hours.

Figure 14:
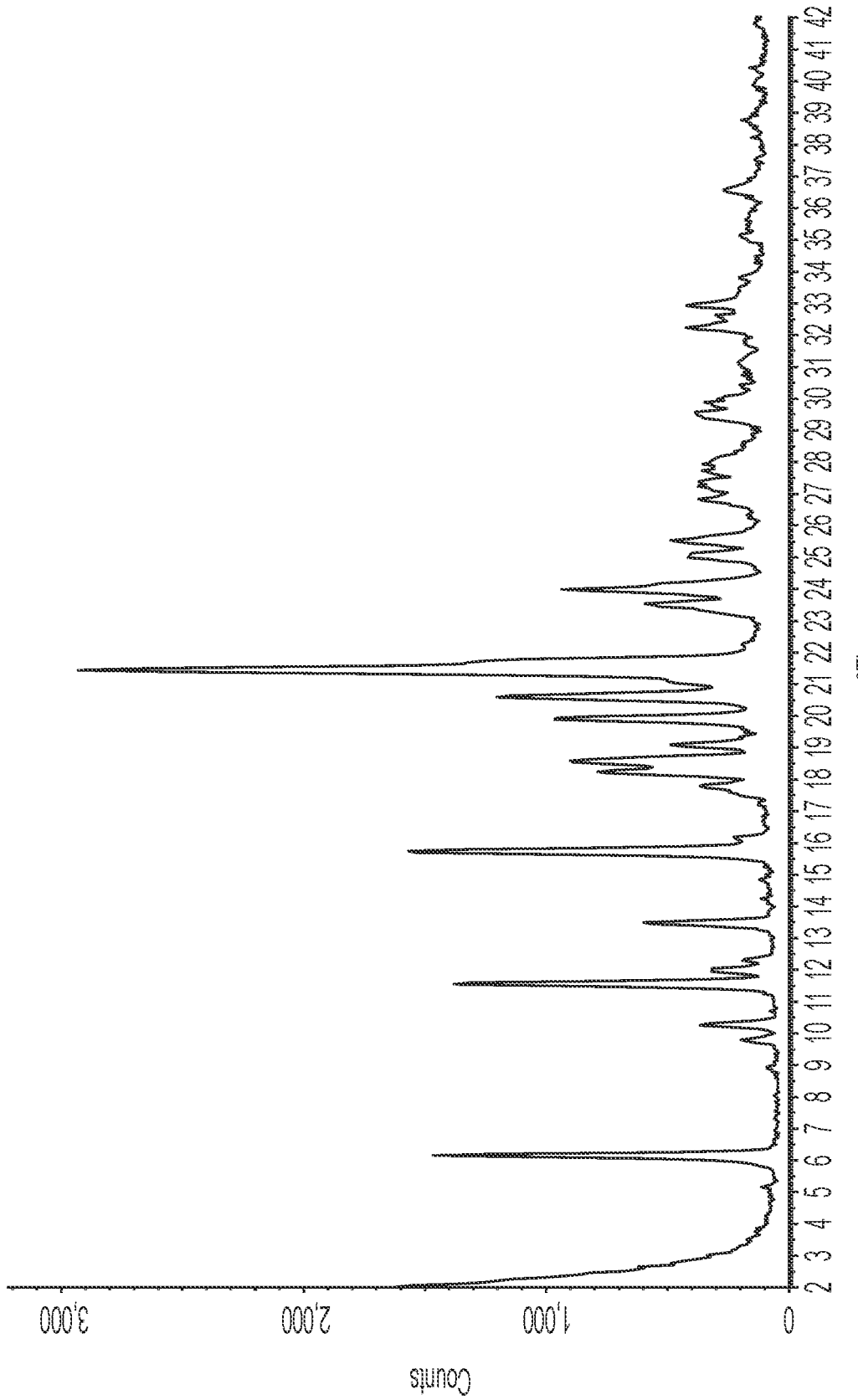
FIG. 14 shows an XRPD pattern of the 2:1 olaparib 2,4-dihydroxybenzoic acid cocrystal.

4.2 XRPD Characterization of the 2:1 Olaparib 2,4-Dihydroxybenzoic Acid Cocrystal The D8 XRPD pattern of the 2:1 olaparib 2,4-dihydroxybenzoic acid cocrystal is shown in FIG. 14. Table 6 lists the angles, °2θ±0.2°2θ, and d value of the peaks identified in the XRPD pattern of FIG. 14. The entire list of peaks or corresponding d values, or a subset thereof, may be sufficient to characterize the cocrystal, as well as by an XRPD pattern substantially similar to FIG. 14. For example, the cocrystal may be characterized by at least two, at least three, at least four, or all of the peaks selected from the peaks at 6.1, 11.6, 13.5, 15.7, and 19.9°2θ±0.2°2θ.

TABLE 6

| Angle °2θ ± 0.2 °2θ | d value Angstrom | Intensity % |
|---|---|---|
| 6.1 | 14.37 | 44% |
| 9.8 | 9.03 | 4% |
| 10.3 | 8.61 | 10% |
| 11.6 | 7.65 | 44% |
| 12.0 | 7.37 | 8% |
| 12.3 | 7.19 | 4% |
| 13.5 | 6.57 | 18% |
| 15.7 | 5.63 | 50% |
| 17.8 | 4.98 | 8% |
| 18.2 | 4.86 | 23% |
| 18.6 | 4.77 | 27% |
| 19.1 | 4.65 | 12% |
| 19.9 | 4.46 | 29% |
| 20.6 | 4.31 | 38% |
| 21.4 | 4.14 | 100% |
| 23.5 | 3.78 | 16% |
| 24.0 | 3.71 | 30% |
| 25.0 | 3.55 | 9% |
| 25.5 | 3.49 | 12% |
| 26.8 | 3.32 | 8% |
| 27.3 | 3.27 | 6% |
| 27.9 | 3.20 | 6% |
| 29.5 | 3.02 | 9% |
| 29.8 | 2.99 | 6% |
| 32.2 | 2.77 | 11% |
| 32.9 | 2.72 | 11% |
| 36.6 | 2.45 | 5% |

Figure 15:
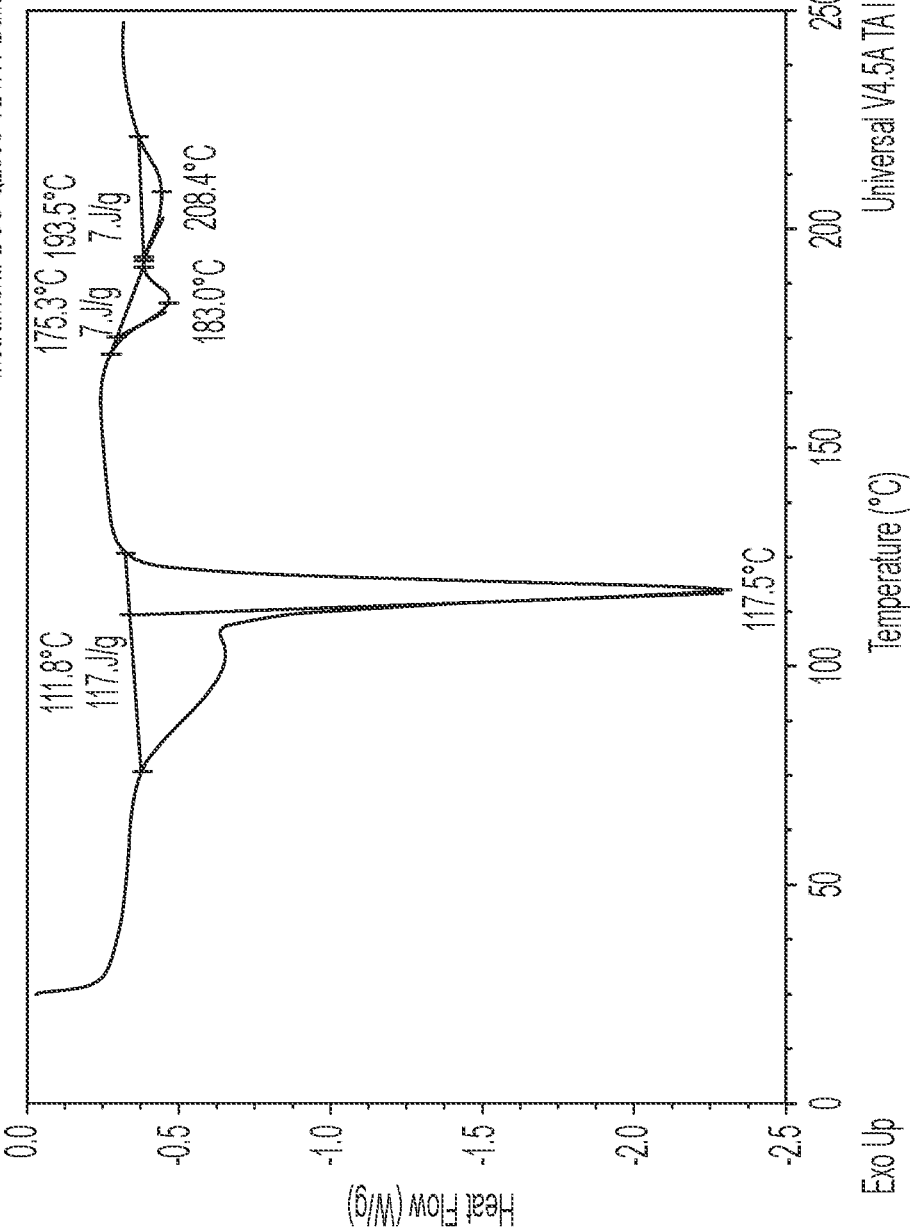
FIG. 15 shows a DSC trace for the 2:1 olaparib 2,4-dihydroxybenzoic acid cocrystal.

TABLE 6-continued 4.3 DSC of the 2:1 Olaparib 2,4-Dihydroxybenzoic Acid Cocrystal The DSC trace of the 2:1 olaparib 2,4-dihydroxybenzoic acid cocrystal as obtained on the TA Q2000 instrument, FIG. 15, shows a major endotherm with an onset temperature of 111.8° C. and a peak maximum of 117.5° C. This is followed by a second endotherm with an onset temperature of 175.3° C. and a peak maximum of 183.0° C. and a third endotherm with an onset temperature of 193.5° C. and a peak maximum of 208.4° C.

4.4 TGA of the 2:1 Olaparib 2,4-Dihydroxybenzoic Acid Cocrystal

Figure 16:
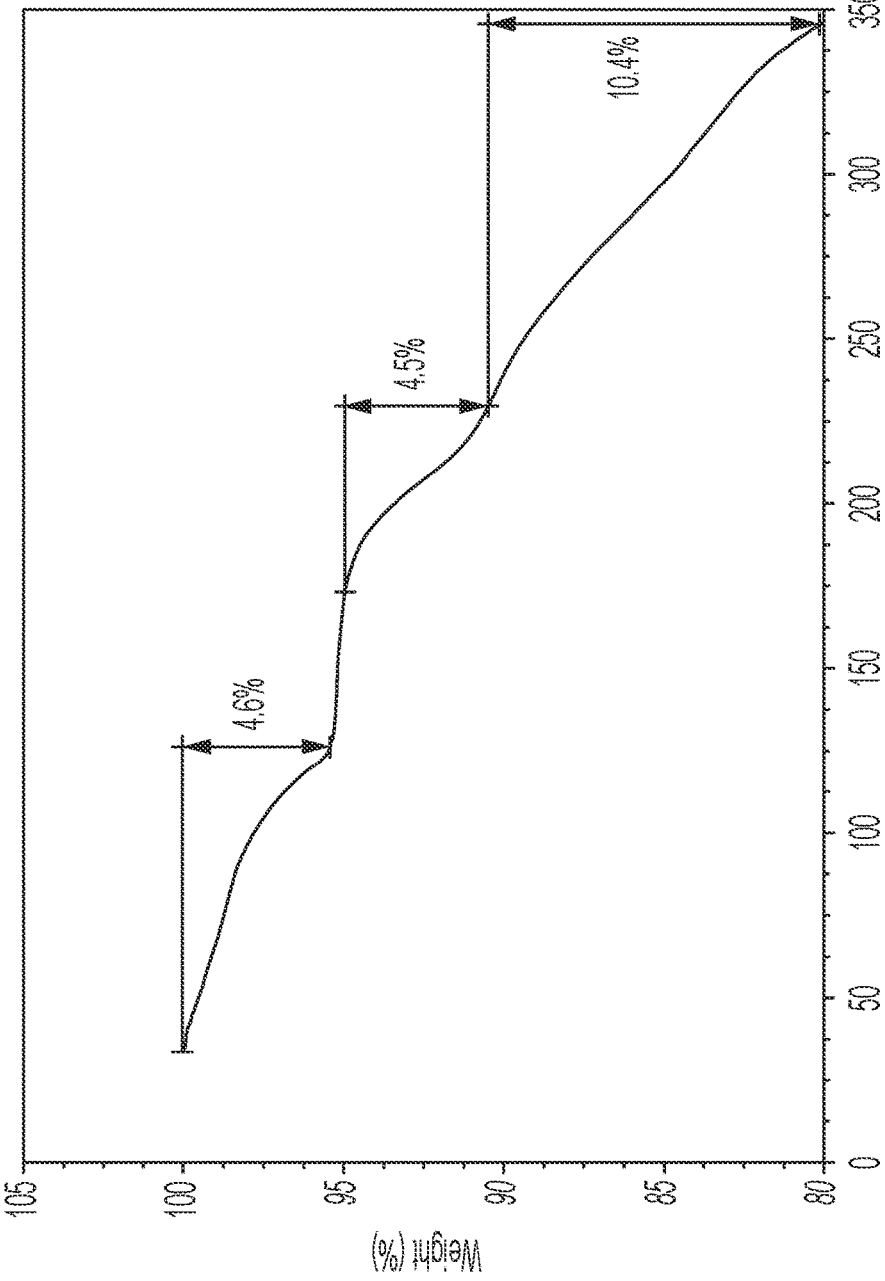
FIG. 16 shows a TGA trace for the 2:1 olaparib 2,4-dihydroxybenzoic acid cocrystal.

In the TGA trace of the 2:1 olaparib 2,4-dihydroxybenzoic acid cocrystal as obtained on the TA Q500 instrument, FIG. 16, there is a weight loss of 4.6% between 40° C. and 125° C.

4.5 Infrared Spectrum of the 2:1 Olaparib 2,4-Dihydroxybenzoic Acid Cocrystal

Figure 17:
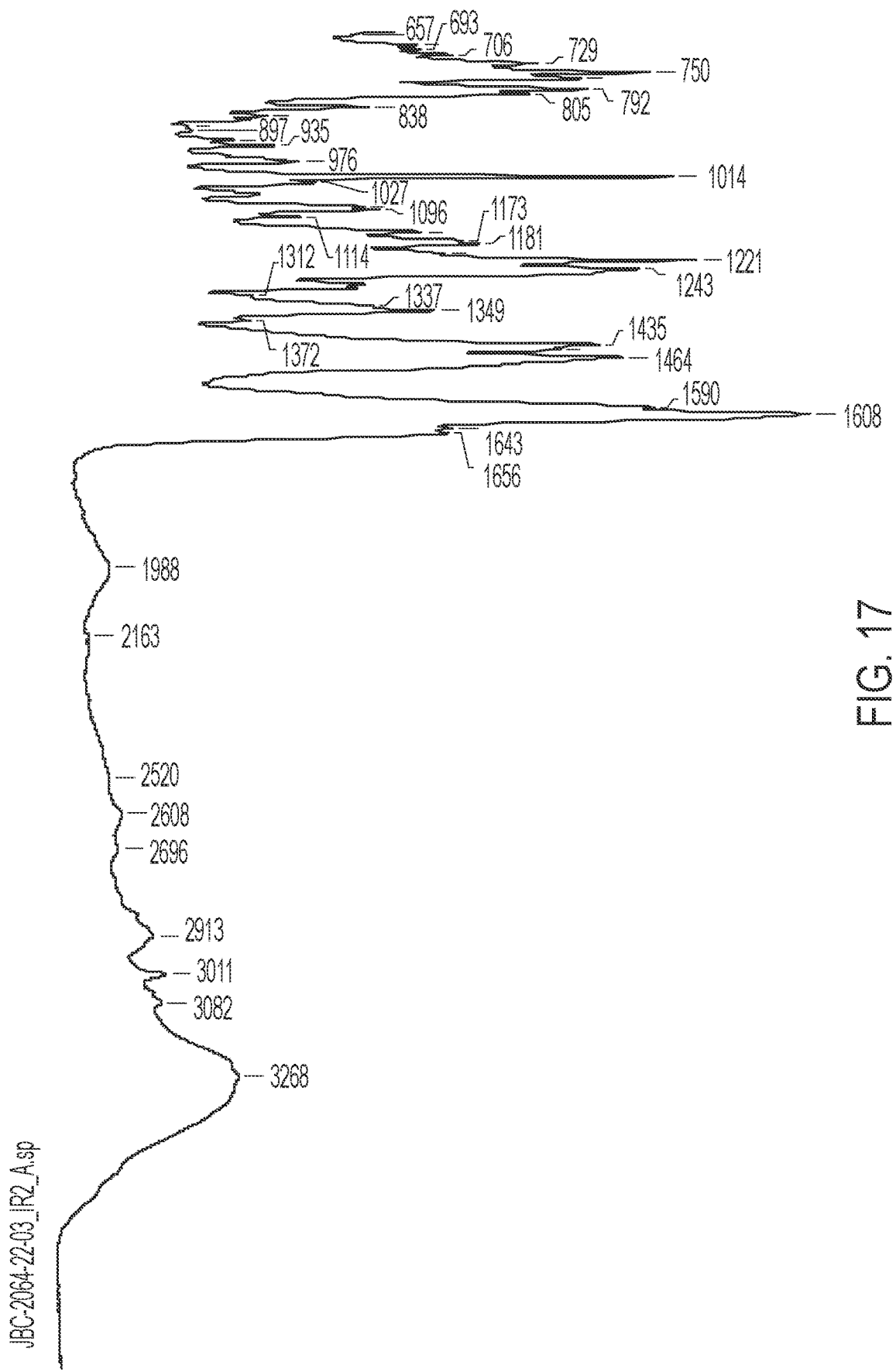
FIG. 17 shows an Infrared spectrum for the 2:1 olaparib 2,4-dihydroxybenzoic acid cocrystal.

The infrared spectrum of the 2:1 olaparib 2,4-dihydroxybenzoic acid cocrystal is shown in FIG. 17. The significant peaks identified in the infrared spectrum of FIG. 17 are 3268, 3011, 1656, 1608, 1590, 1464, 1435, 1349, 1337, 1243, 1221, 1181, 1173, 1114, 1096, 1027, 1014, 976, 936, 838, 805, 797, 750, 729, 706, 693, and 657 $cm^{-1} \pm 1\ cm^{-1}$. The entire list of peaks, or a subset thereof, may be sufficient to characterize the cocrystal, as well as by an infrared pattern substantially similar to FIG. 17. For example, the cocrystal may be characterized by at least two, at least three, at least four, or all of the peaks selected from the peaks at 1014, 1222, 1243, 1435, and 1590 $cm^{-1} \pm 1\ cm^{-1}$.

Figure 18:
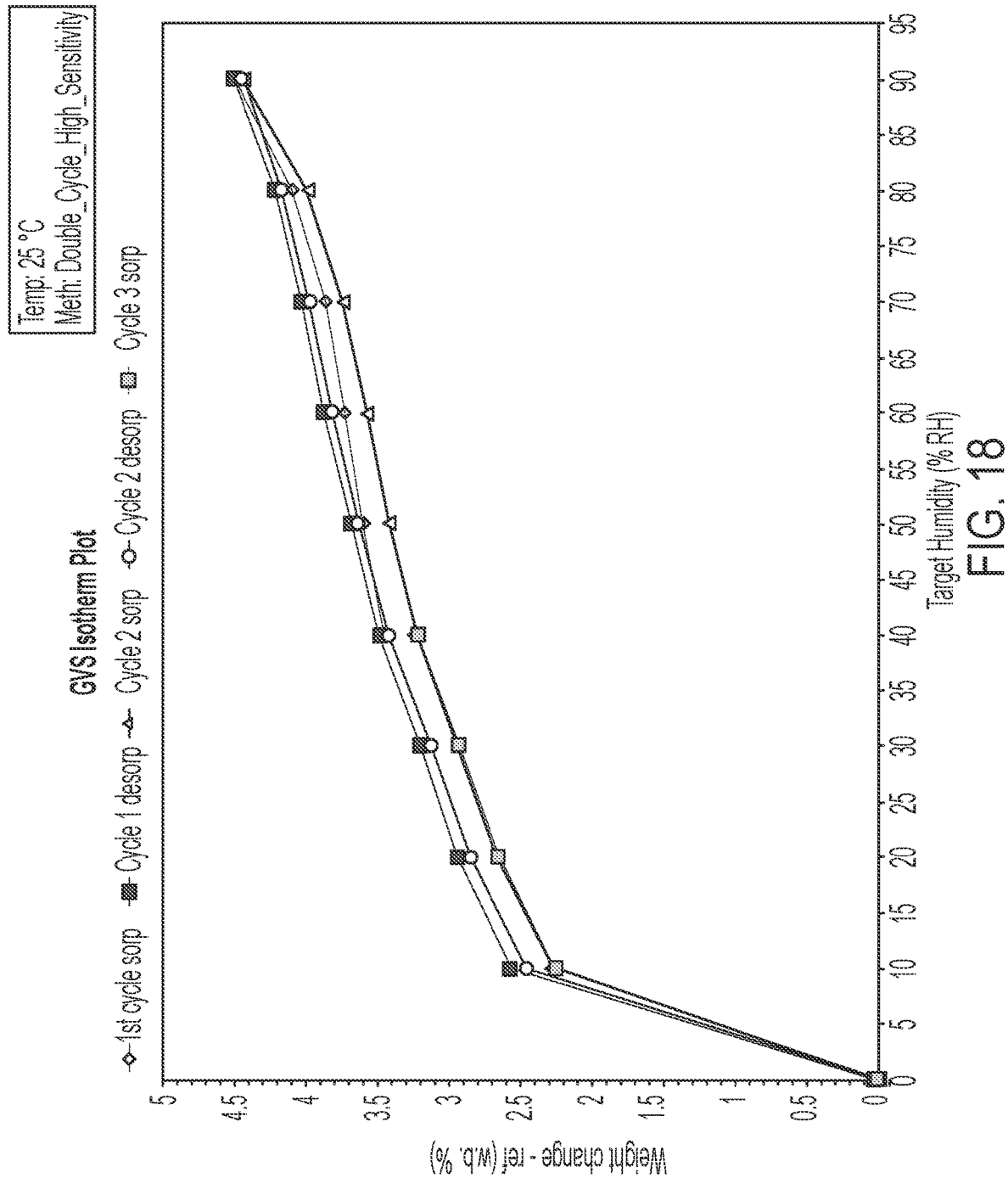
FIG. 18 shows a GVS isotherm graph for the 2:1 olaparib 2,4-dihydroxybenzoic acid cocrystal.

4.6 Gravimetric Vapour Sorption (GVS) Analysis of the 2:1 Olaparib 2,4-Dihydroxybenzoic Acid Cocrystal The moisture sorption isotherm graph obtained for the 2:1 olaparib 2,4-dihydroxybenzoic acid cocrystal is shown in FIG. 18. The cocrystal was found to reversibly absorb 4.5% w/w across the 0-90% relative humidity range at 25° C. under nitrogen (2.5% w/w was reversibly absorbed between 0 and 5% RH). XRPD analysis of the sample post GVS confirmed that the cocrystal structure was unchanged.

4.7 Karl Fischer Titration of the 2:1 Olaparib 2,4-Dihydroxybenzoic Acid Cocrystal Karl Fischer analysis of the 2:1 olaparib 2,4-dihydroxybenzoic acid cocrystal indicated that the sample contained 5.5% water, which is equivalent to 3.2 moles of water.

Example 5

2:1 Olaparib 4-Hydroxybenzoic Acid Cocrystal 5.1 Preparation of the 2:1 Olaparib 4-Hydroxybenzoic Acid Cocrystal The batch of 2:1 olaparib 4-hydroxybenzoic acid cocrystal used for characterization was prepared as follows:

Olaparib (500 mg, 1.15 mmol) and 4-hydroxybenzoic acid (79 mg, 0.57 mmol) were milled together with water (200 µL) for 3×20 minutes at 30 Hz in a Retsch MM400 ball mill. The product was dried in-vacuo at 40° C. for 2 hours.

5.2 XRPD Characterization of the 2:1 Olaparib 4-Hydroxybenzoic Acid Cocrystal

Figure 19:
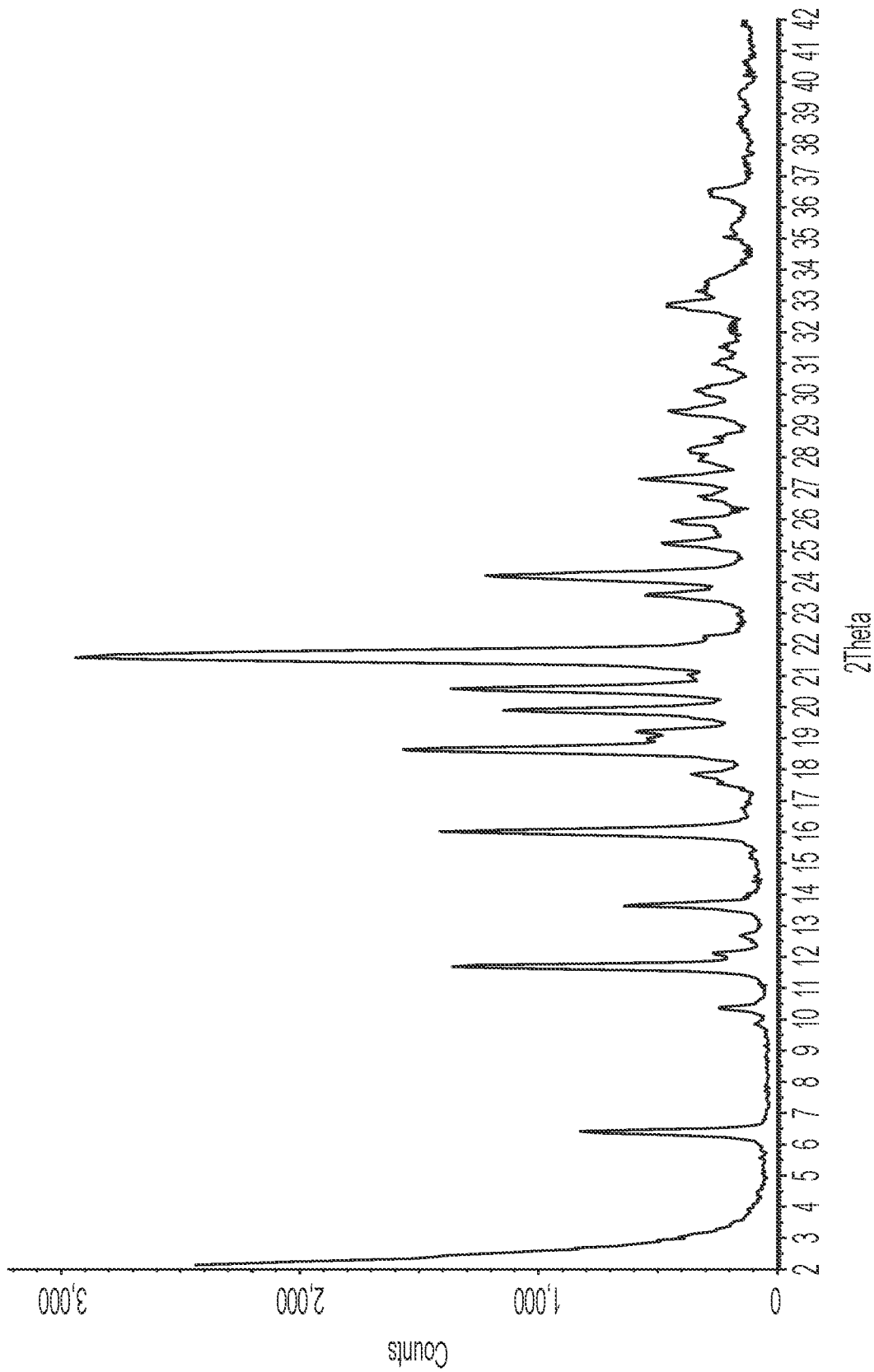
FIG. 19 shows an XRPD pattern of the 2:1 olaparib 4-hydroxybenzoic acid cocrystal.

The D8 XRPD pattern of the 2:1 olaparib 4-hydroxybenzoic acid cocrystal is shown in FIG. 19. Table 7 lists the angles, °2θ±0.2°2θ, and d value of the peaks identified in the XRPD pattern of FIG. 19. The entire list of peaks or corresponding d values, or a subset thereof, may be sufficient to characterize the cocrystal, as well as by an XRPD pattern substantially similar to FIG. 19. For example, the cocrystal may be characterized by at least two, at least three, at least four, or all of the peaks selected from the peaks at 6.3, 13.6, 15.9, 19.8, and 21.6°2θ±0.2°2θ.

TABLE 7

| Angle<br>°2θ ± 0.2 °2θ | d value<br>Angstrom | Intensity<br>% |
|---|---|---|
| 6.3 | 14.06 | 24% |
| 10.3 | 8.62 | 6% |
| 11.6 | 7.62 | 44% |
| 12.0 | 7.35 | 11% |
| 13.6 | 6.52 | 19% |
| 15.9 | 5.56 | 48% |
| 17.8 | 4.99 | 8% |
| 18.6 | 4.77 | 51% |
| 18.9 | 4.69 | 22% |
| 19.2 | 4.63 | 25% |
| 19.8 | 4.47 | 37% |
| 20.5 | 4.32 | 44% |
| 21.6 | 4.12 | 100% |
| 23.6 | 3.77 | 15% |
| 24.2 | 3.68 | 40% |
| 25.2 | 3.53 | 12% |
| 25.9 | 3.43 | 15% |
| 26.7 | 3.33 | 8% |
| 27.3 | 3.27 | 15% |
| 28.2 | 3.16 | 11% |
| 29.5 | 3.03 | 11% |
| 30.1 | 2.96 | 7% |
| 32.9 | 2.72 | 12% |

5.3 DSC of the 2:1 Olaparib 4-Hydroxybenzoic Acid Cocrystal

Figure 20:
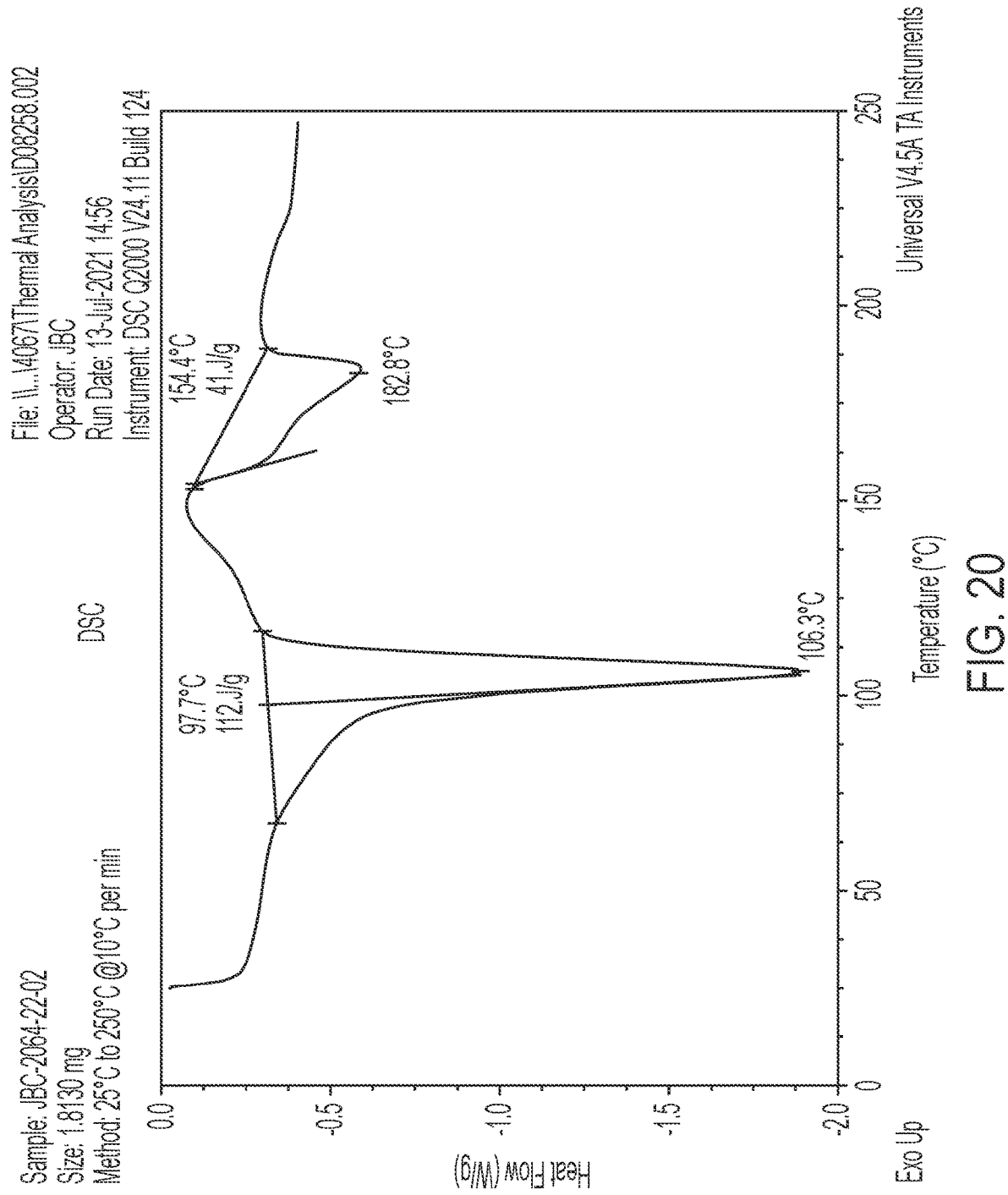
FIG. 20 shows a DSC trace for the 2:1 olaparib 4-hydroxybenzoic acid cocrystal.

The DSC trace of the 2:1 olaparib 4-hydroxybenzoic acid cocrystal as obtained on the TA Q2000 instrument, FIG. 20, shows a major endotherm with an onset temperature of 97.7° C. and a peak maximum of 106.3° C. followed by a second broad endotherm with an onset temperature of 154.4° C. and a peak maximum of 182.8° C.

5.4 TGA of the 2:1 Olaparib 4-Hydroxybenzoic Acid Cocrystal

Figure 21:
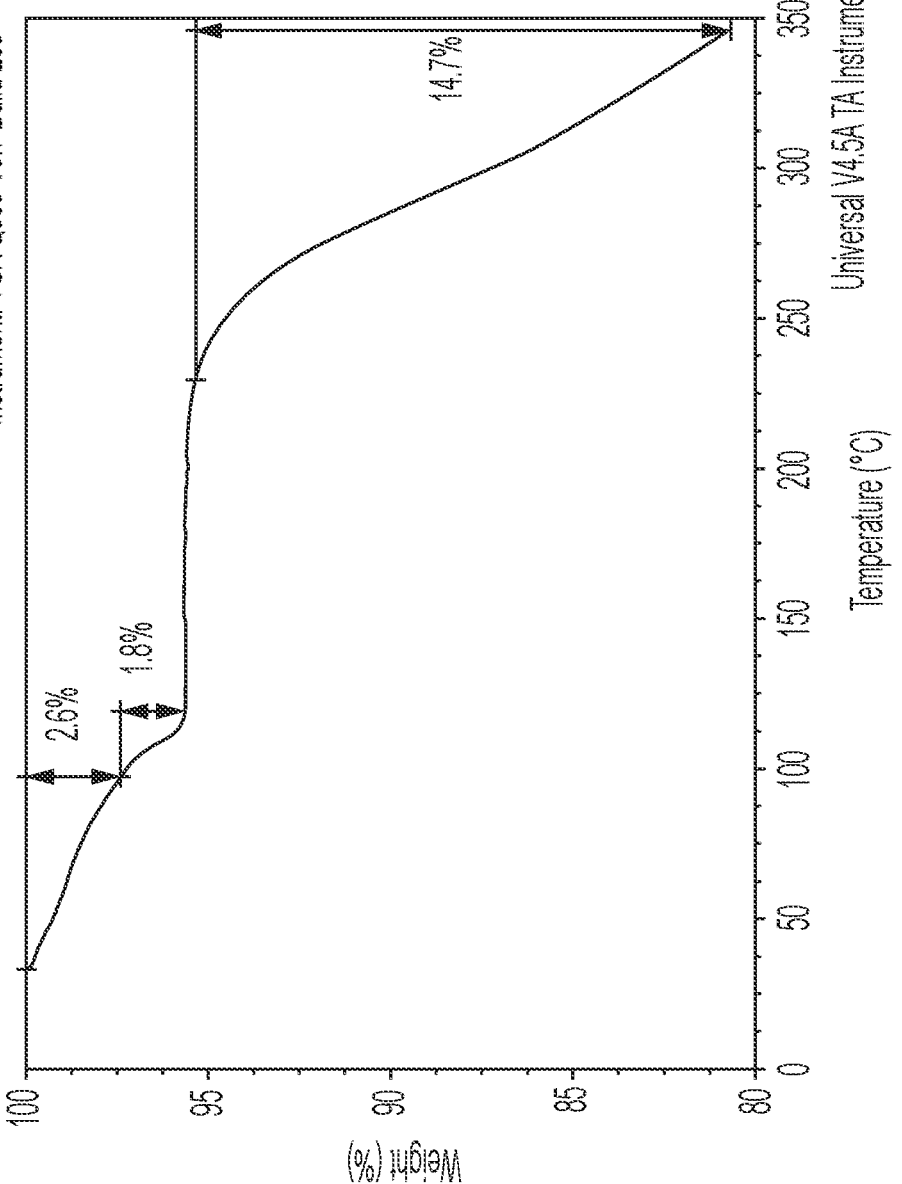
FIG. 21 shows a TGA trace for the 2:1 olaparib 4-hydroxybenzoic acid cocrystal.

In the TGA trace of the 2:1 olaparib 4-hydroxybenzoic acid cocrystal as obtained on the TA Q500 instrument, FIG. 21, there is a weight loss of 4.4% between room temperature and 120° C.

5.5 Infrared Spectrum of the 2:1 Olaparib 4-Hydroxybenzoic Acid Cocrystal

Figure 22:
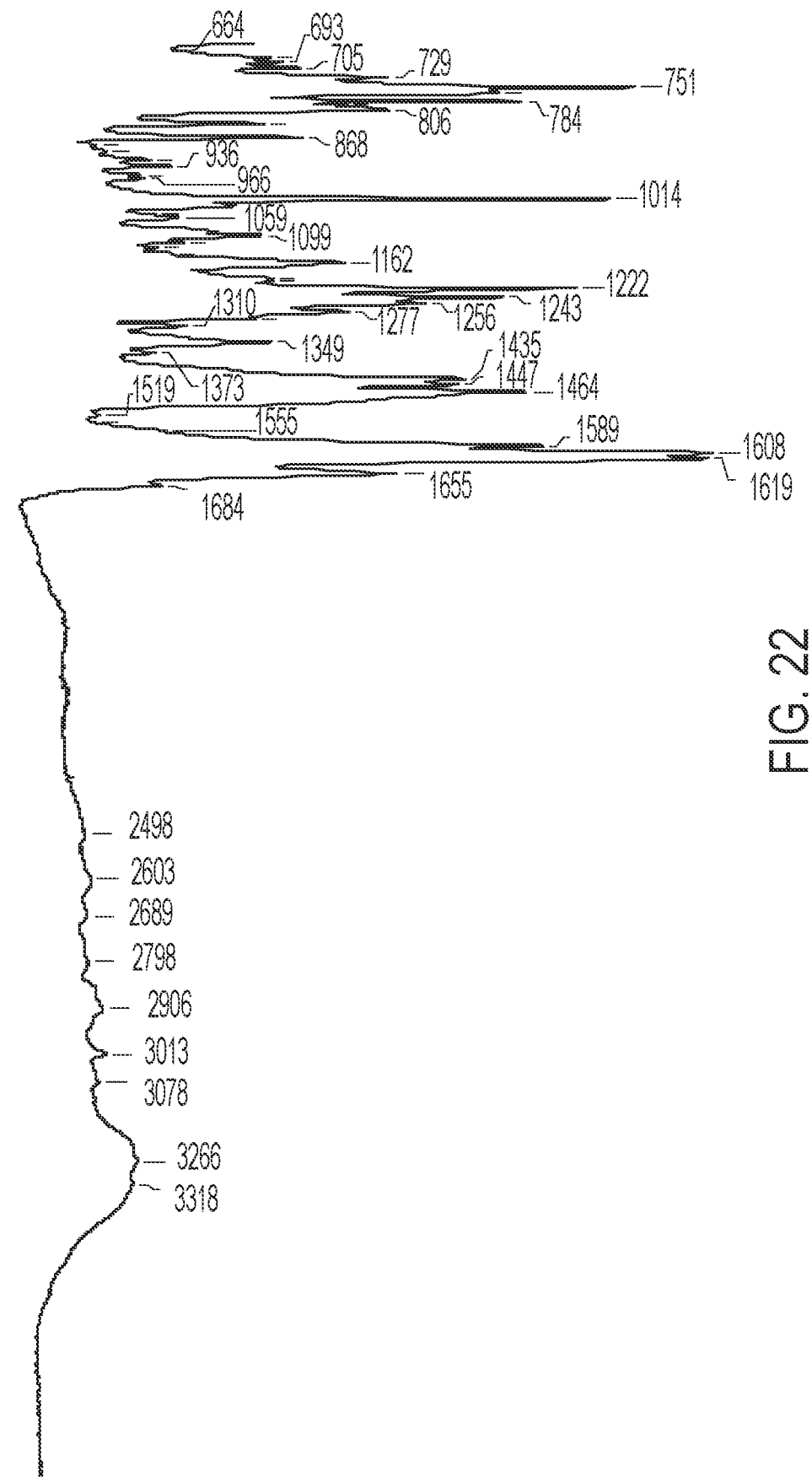
FIG. 22 shows an Infrared spectrum for the 2:1 olaparib 4-hydroxybenzoic acid cocrystal.

The infrared spectrum of the 2:1 olaparib 4-hydroxybenzoic acid cocrystal is shown in FIG. 22. The significant peaks identified in the infrared spectrum of FIG. 22 are 3266, 1684, 1655, 1619, 1608, 1589, 1464, 1447, 1435, 1373, 1349, 1310, 1277, 1256, 1243, 1222, 162, 1099, 1059, 936, 868, 806, 784, 751, 729, 705, 693, and 664 cm$^{-1}$±1 cm$^{-1}$. The entire list of peaks, or a subset thereof, may be sufficient to characterize the cocrystal, as well as by an infrared pattern substantially similar to FIG. 22. For example, the cocrystal may be characterized by at least two, at least three, at least four, or all of the peaks selected from the peaks at 1014, 1222, 1243, 1435, and 1590 cm$^{-1}$±1 cm$^{-1}$.

Figure 23:
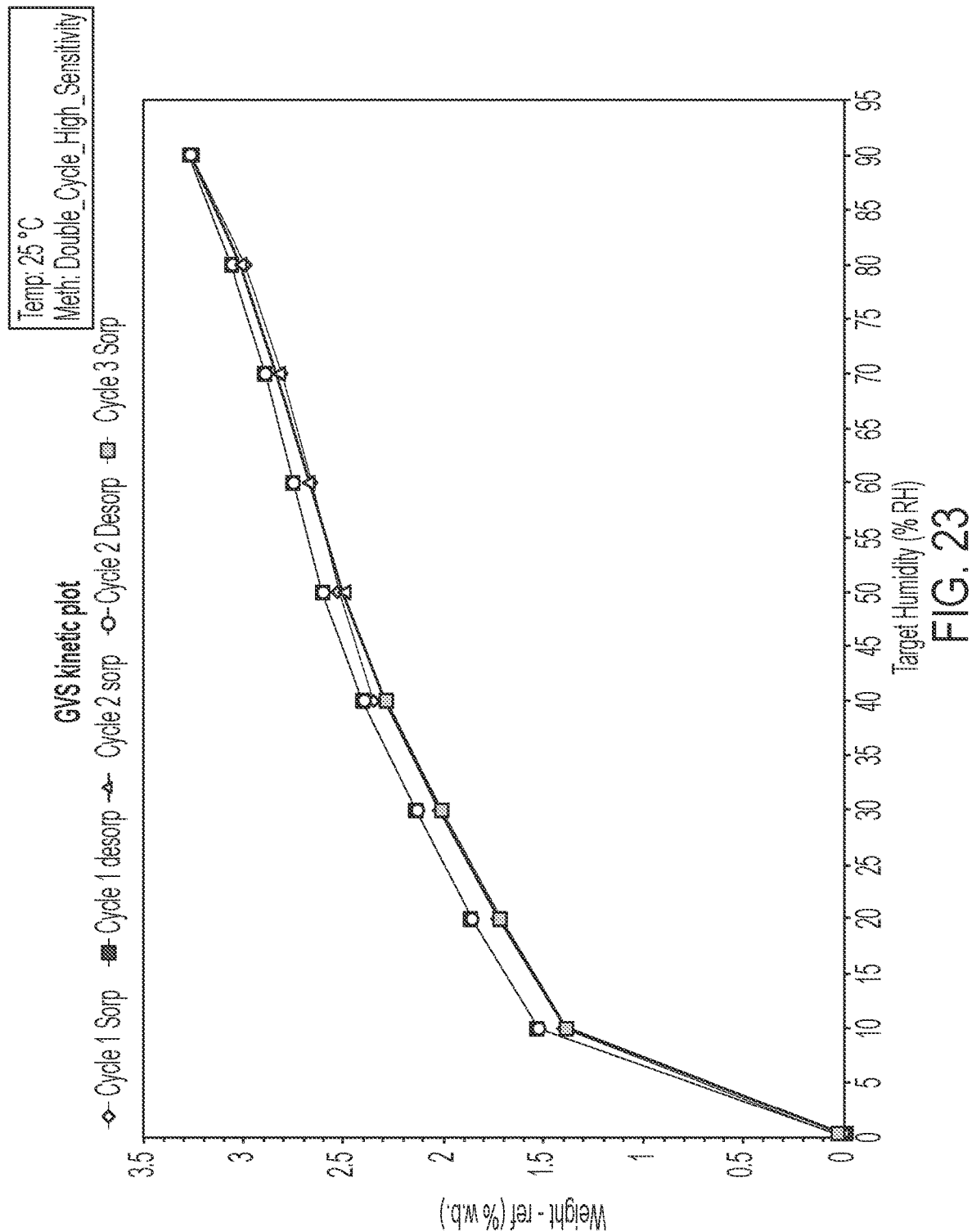
FIG. 23 shows a GVS isotherm graph for the 2:1 olaparib 4-hydroxybenzoic acid cocrystal.

5.6 Gravimetric Vapour Sorption (GVS) Analysis of the 2:1 Olaparib 4-Hydroxybenzoic Acid Cocrystal The moisture sorption isotherm graph obtained for the 2:1 olaparib 4-hydroxybenzoic acid cocrystal is shown in FIG. 23. The cocrystal was found to reversibly absorb 3.4% w/w across the 0-90% relative humidity range at 25° C. under nitrogen (1.5% w/w was reversibly absorbed between 0 and 5% RH). XRPD analysis of the sample post GVS confirmed that the cocrystal structure was unchanged.

5.7 Karl Fischer Titration of the 2:1 Olaparib 4-Hydroxybenzoic Acid Cocrystal

Karl Fischer analysis of the 2:1 olaparib 4-hydroxybenzoic acid cocrystal indicated that the sample contained 4.8% water, which is equivalent to 2.9 moles of water.

Example 6

1:1 Olaparib Salicylic Acid Cocrystal 6.1 Preparation of the 1:1 Olaparib Salicylic Acid Cocrystal The batch of crystalline 1:1 olaparib salicylic acid cocrystal used for characterization was prepared as follows:

Olaparib (208 mg, 048 mmol) and salicylic acid (66 mg, 0.48 mmol) were milled together with nitromethane (3 drops) for 5×15 minutes at 30 Hz in a Retsch M M400 ball mill. The product was dried in-vacuo at 40° C. for 1 hour.

6.2 XRPD Characterization of the 1:1 Olaparib Salicylic Acid Cocrystal

Figure 24:
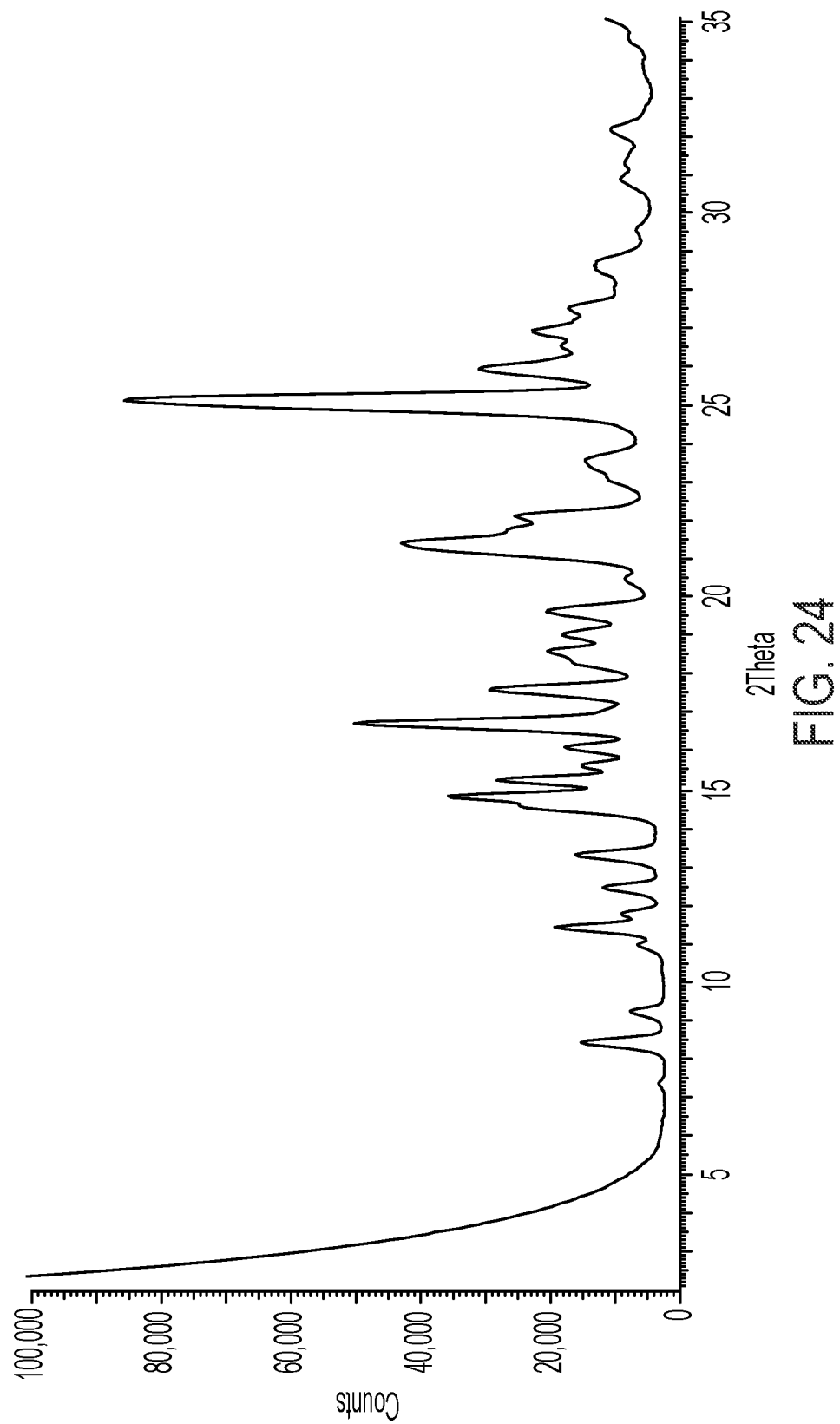
FIG. 24 shows an XRPD pattern of the 1:1 olaparib salicylic acid cocrystal.

The D2 XRPD pattern of the 1:1 olaparib salicylic acid cocrystal is shown in FIG. 24. Table 8 lists the angles, °2θ±0.2°2θ, and d value of the peaks identified in the XRPD pattern of FIG. 24. The entire list of peaks or corresponding d values, or a subset thereof, may be sufficient to characterize the cocrystal, as well as by an XRPD pattern substantially similar to FIG. 24. For example, the cocrystal may be characterized by at least two, at least three, at least four, or all of the peaks selected from the peaks at 8.4, 9.3, 12.5, 13.3, and 16.7°2θ±0.2°2θ.

TABLE 8

| Angle<br>°2θ ± 0.2 °2θ | d value<br>Angstrom | Intensity<br>% |
|---|---|---|
| 8.4 | 10.46 | 13.7% |
| 9.3 | 9.55 | 5.3% |
| 11.4 | 7.72 | 18.2% |
| 11.8 | 7.51 | 6.2% |
| 12.5 | 7.09 | 9.4% |
| 13.3 | 6.64 | 14.2% |
| 14.6 | 6.05 | 24.1% |
| 14.8 | 5.97 | 37.1% |
| 15.3 | 5.80 | 28.3% |
| 15.6 | 5.66 | 12.3% |
| 16.1 | 5.50 | 15.4% |
| 16.7 | 5.29 | 54.7% |
| 17.6 | 5.03 | 29.3% |
| 18.6 | 4.77 | 18.5% |
| 19.0 | 4.66 | 15.5% |
| 19.6 | 4.52 | 18.7% |
| 21.4 | 4.15 | 46.9% |
| 21.7 | 4.09 | 25.8% |
| 22.1 | 4.02 | 24.6% |
| 23.6 | 3.77 | 10.6% |
| 25.1 | 3.54 | 100.0% |
| 25.9 | 3.43 | 31.5% |
| 26.5 | 3.36 | 15.7% |
| 26.9 | 3.31 | 21.3% |
| 27.5 | 3.24 | 14.6% |
| 28.7 | 3.11 | 9.4% |
| 30.9 | 2.90 | 5.8% |

TABLE 8-continued

| Angle °2θ ± 0.2 °2θ | d value Angstrom | Intensity % |
|---|---|---|
| 31.3 | 2.86 | 4.8% |
| 32.1 | 2.78 | 7.7% |

6.3 DSC of the 1:1 Olaparib Salicylic Acid Cocrystal

Figure 25:
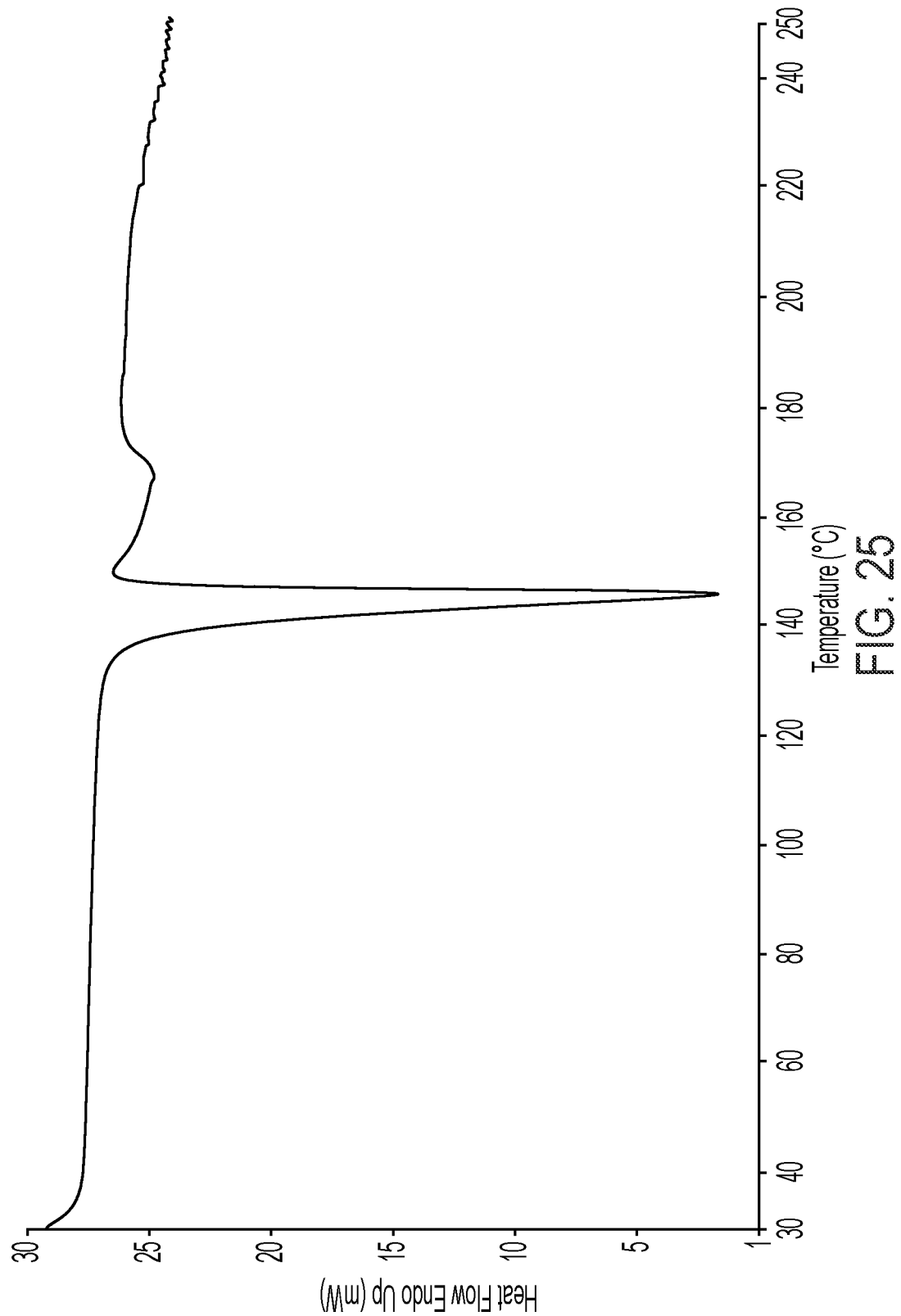
FIG. 25 shows a DSC trace for the 1:1 olaparib salicylic acid cocrystal.

The DSC trace of the 1:1 olaparib salicylic acid cocrystal as obtained on the Pyris 4000 instrument, FIG. 25, shows a major endotherm with a peak maximum of 146.4° C.

6.4 TGA of the 1:1 Olaparib Salicylic Acid Cocrystal

Figure 26:
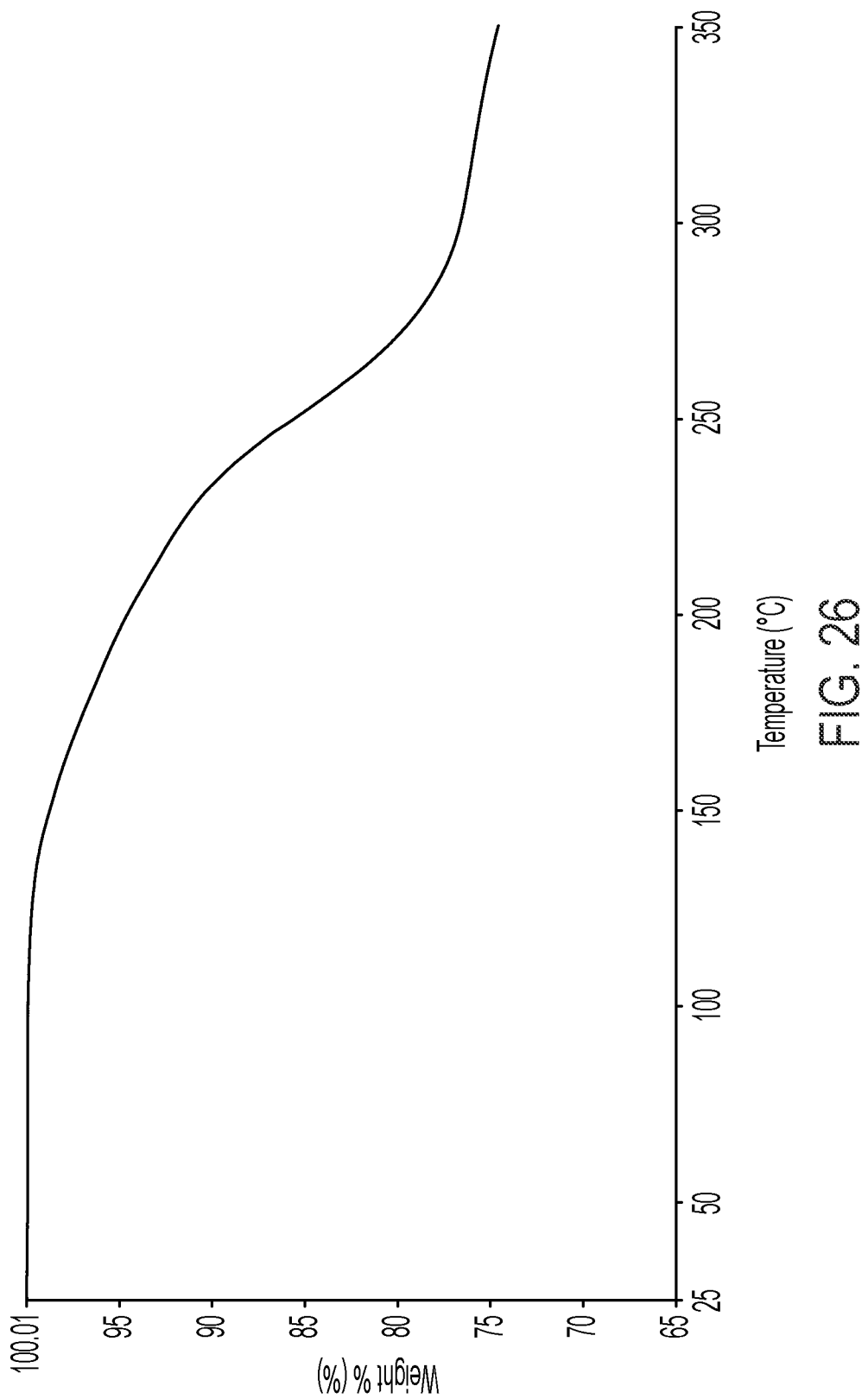
FIG. 26 shows a TGA trace for the 1:1 olaparib salicylic acid cocrystal.

In the TGA trace of the 1:1 olaparib salicylic acid cocrystal as obtained on the Perkin Elmer 4000 instrument, FIG. 26, there is no significant weight loss until after 150° C., at which point a 24% weight loss is observed, which corresponds to the loss of 1 mole of salicylic acid. This shows that the cocrystal has 1:1 olaparib:salicylic acid stoichiometry and that the cocrystal is anhydrous.

Example 7

1:1 Olaparib 3,4-Dihydroxybenzoic Acid Cocrystal 7.1 Preparation of the 1:1 Olaparib 3,4-Dihydroxybenzoic Acid Cocrystal The batch of crystalline 1:1 olaparib 3,4-dihydroxybenzoic acid cocrystal used for characterization was prepared as follows:

Olaparib (74 mg, 0.17 mmol) and 3,4-dihydroxybenzoic acid (26 mg, 0.17 mmol) were placed in a glass vial and water (3 ml) saturated with 3,4-dihydroxybenzoic acid was added. The resulting slurry was placed in a shaker and matured for 2 days (room temperature to 50° C. on an 8 hour cycle, heating to 50° C. for 4 hours and then cooling to RT for a further 4 hours). The product was then filtered under vacuum and dried in-vacuo at 40° C. for 8 hours.

Figure 27:
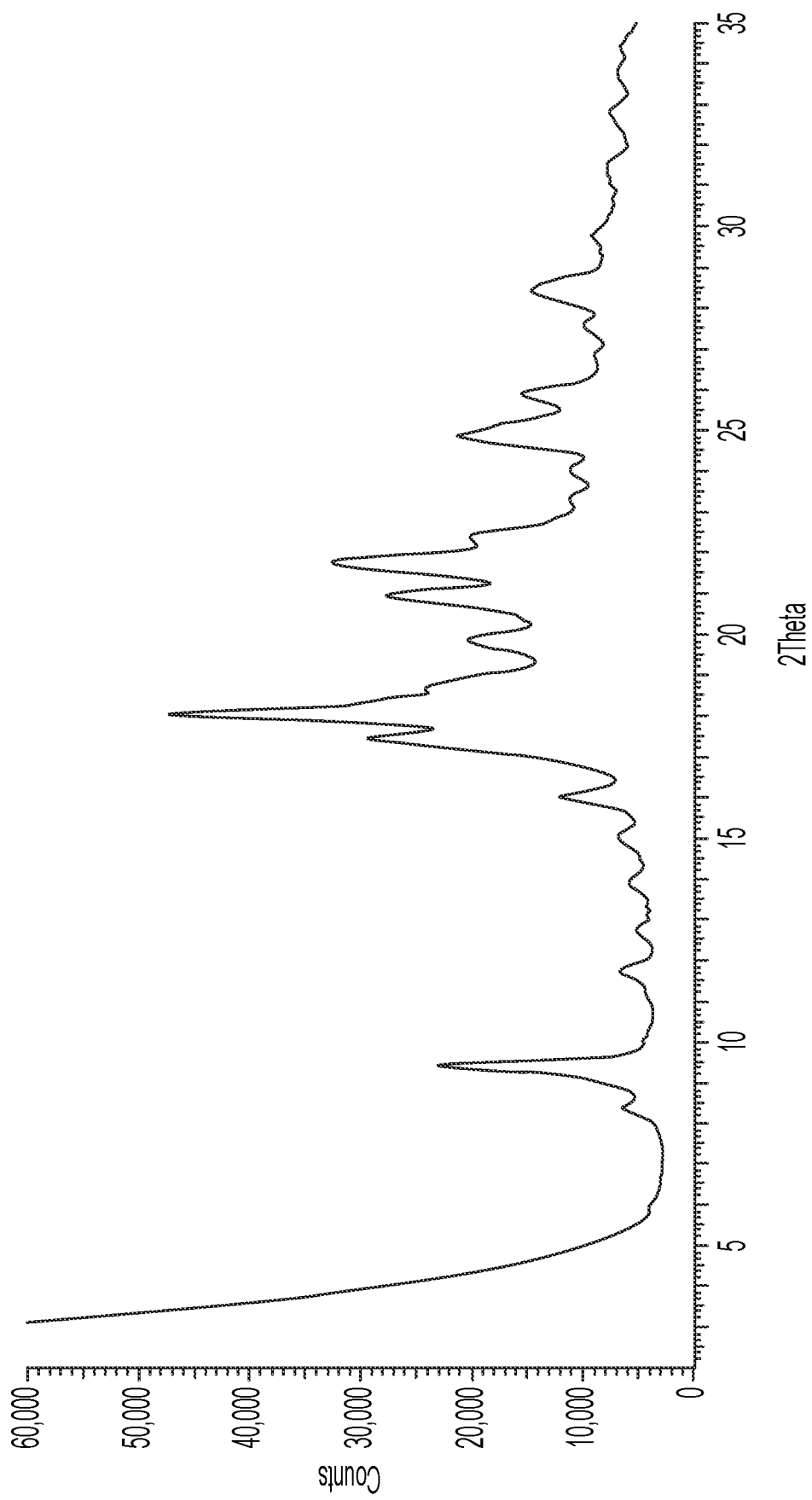
FIG. 27 shows an XRPD pattern of the 1:1 olaparib 3,4-dihydroxybenzoic acid cocrystal.

7.2 XRPD Characterization of the 1:1 Olaparib 3,4-Dihydroxybenzoic Acid Cocrystal The D2 XRPD pattern of the 1:1 olaparib 3,4-dihydroxybenzoic acid cocrystal as acquired on the Bruker 2nd Gen D2-Phaser diffractometer is shown in FIG. 27. Table 9 lists the angles, °2θ±0.2°2θ, and d value of the peaks identified in the XRPD pattern of FIG. 27. The entire list of peaks or corresponding d values, or a subset thereof, may be sufficient to characterize the cocrystal, as well as by an XRPD pattern substantially similar to FIG. 27. For example, the cocrystal may be characterized by at least two, at least three, at least four, or all of the peaks selected from the peaks at 9.4, 11.7, 16.0, 17.4, and 19.9°2θ±0.2°2θ.

TABLE 9

| Angle °2θ ± 0.2 °2θ | d value Angstrom | Intensity % |
|---|---|---|
| 8.4 | 10.54 | 7.6% |
| 9.4 | 9.38 | 52.7% |
| 11.7 | 7.53 | 7.2% |
| 12.8 | 6.93 | 2.8% |
| 13.9 | 6.35 | 3.6% |
| 15.0 | 5.9 | 4.1% |
| 16.0 | 5.53 | 18.5% |
| 17.4 | 5.08 | 68.2% |
| 18.2 | 4.87 | 100.0% |
| 18.7 | 4.75 | 78.9% |
| 19.9 | 4.47 | 38.9% |
| 20.9 | 4.24 | 61.6% |
| 21.7 | 4.09 | 74.9% |
| 22.2 | 4.01 | 34.9% |
| 23.3 | 3.81 | 8.7% |
| 24.0 | 3.71 | 8.7% |
| 24.8 | 3.58 | 40.3% |
| 25.9 | 3.44 | 21.9% |
| 27.6 | 3.23 | 6.3% |
| 28.4 | 3.14 | 22.1% |

7.3 DSC of the 1:1 Olaparib 3,4-Dihydroxybenzoic Acid Cocrystal

Figure 28:
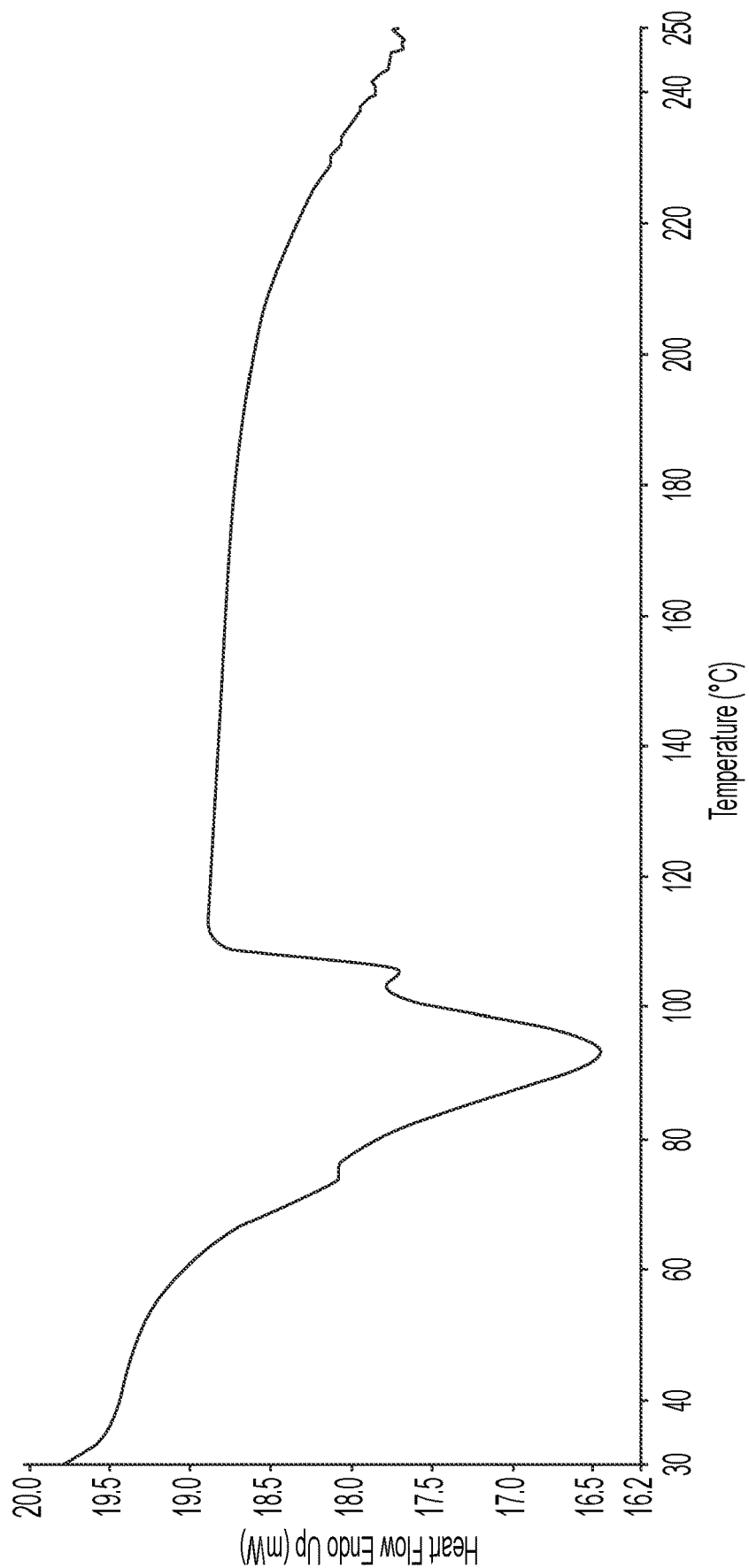
FIG. 28 shows a DSC trace for the 1:1 olaparib 3,4-dihydroxybenzoic acid cocrystal.

The DSC trace of the 1:1 olaparib 3,4-dihydroxybenzoic acid cocrystal as obtained on the Pyris 4000 instrument, FIG. 28, shows a broad endotherm with a peak maximum at 93.2° C. The broad endotherm shows two smaller shoulder peaks at temperatures above and below the temperature of the peak maximum.

7.4 TGA of the 1:1 Olaparib 3,4-Dihydroxybenzoic Acid Cocrystal

Figure 29:
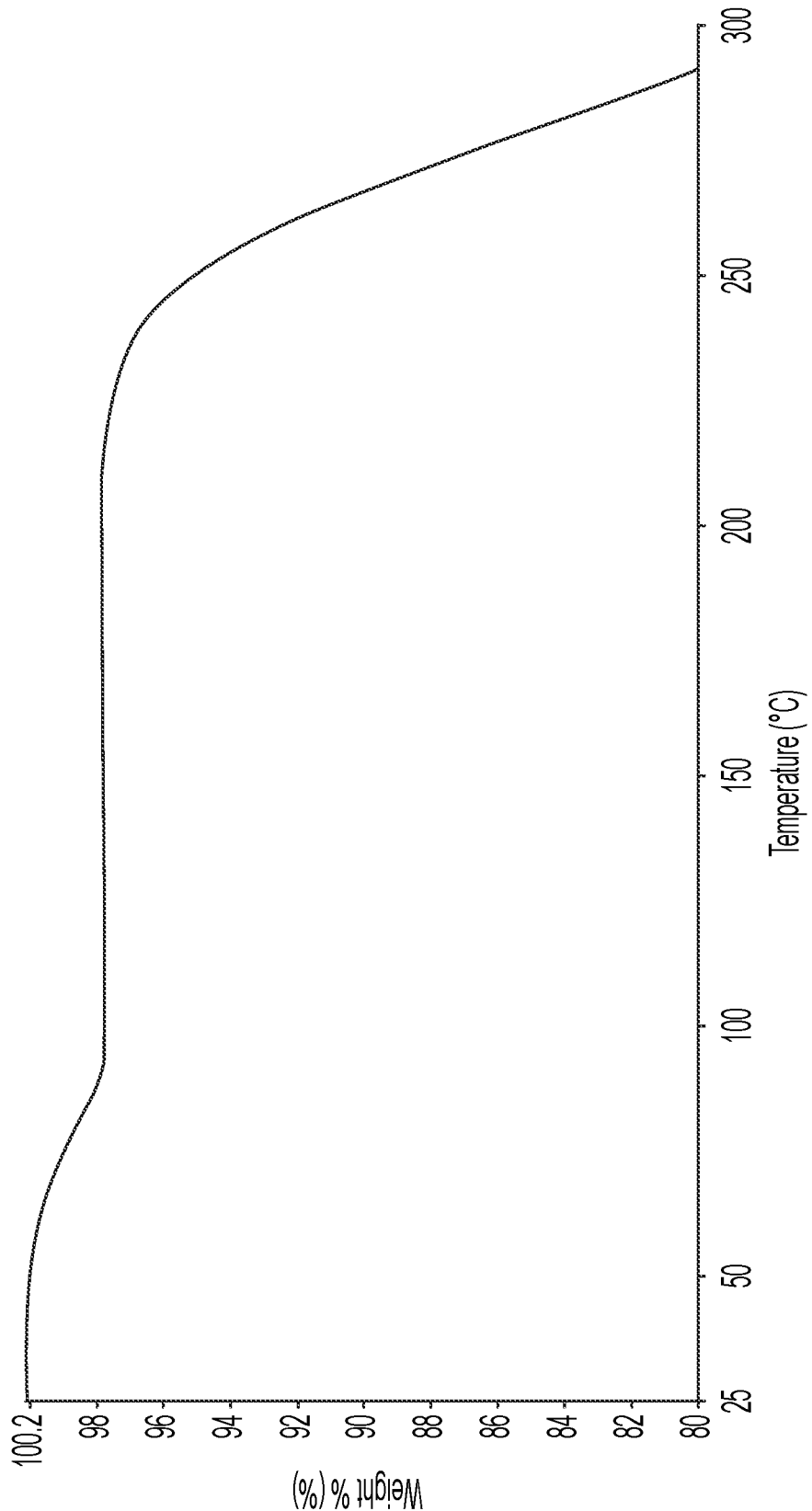
FIG. 29 shows a TGA trace for the 1:1 olaparib 3,4-dihydroxybenzoic acid cocrystal.

In the TGA trace of the 1:1 olaparib 3,4-dihydroxybenzoic acid cocrystal as obtained on the Perkin Elmer 4000 instrument, FIG. 29, there is a weight loss of approximately 2.3% between 45° C. and 95° C. which corresponds to 0.8 mols of water suggesting that there is water trapped within the crystal structure of the 1:1 Olaparib 3,4-Dihydroxybenzoic Acid Cocrystal.

7.5 $^1$H NMR Spectrum of the 1:1 Olaparib 3,4-Dihydroxybenzoic Acid Cocrystal

Figure 30:
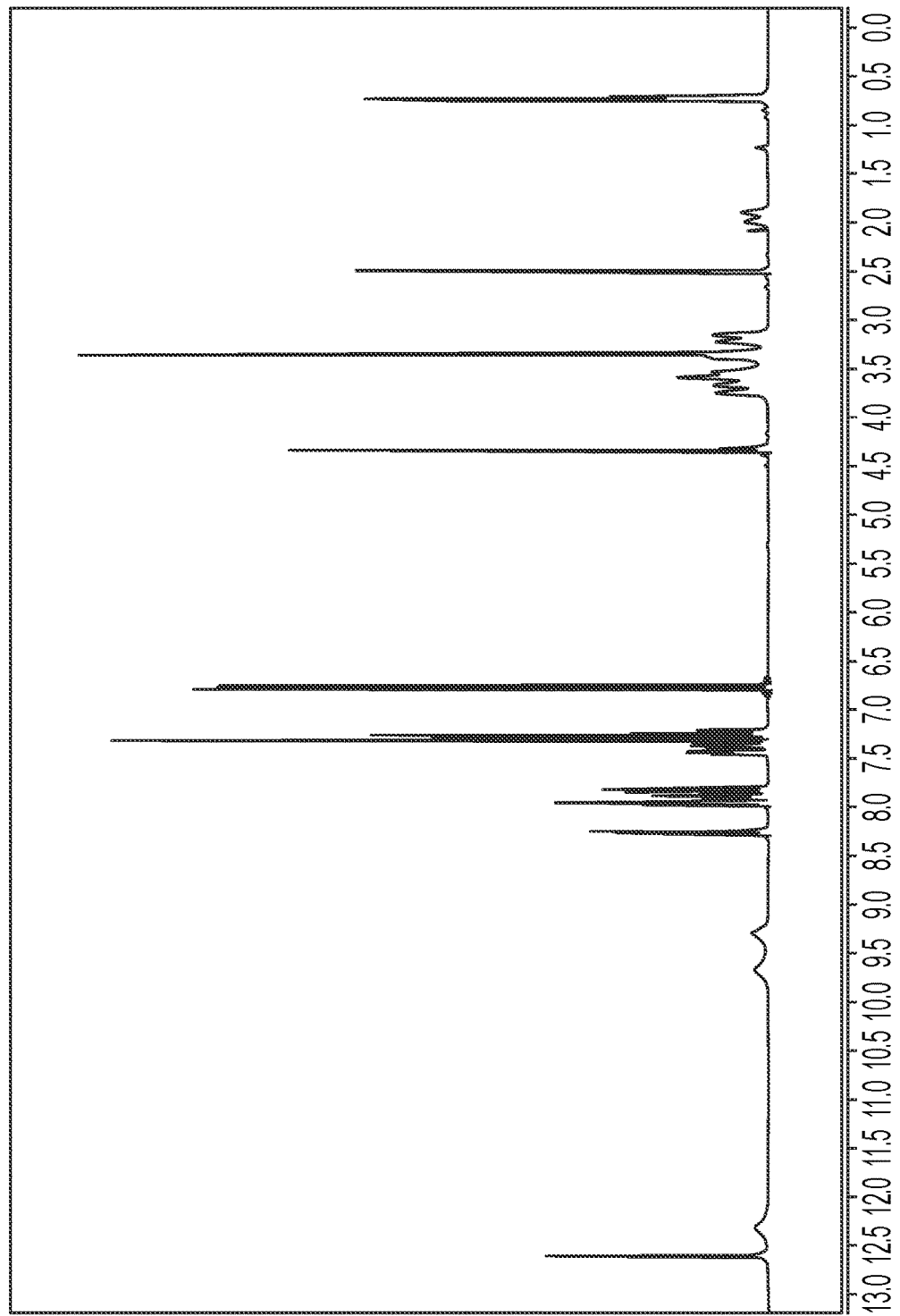
FIG. 30 shows the $^1$H NMR spectrum for the 1:1 olaparib 3,4-dihydroxybenzoic acid cocrystal.

The $^1$H NMR spectrum of the 1:1 olaparib 3,4-dihydroxybenzoic acid cocrystal, shown in FIG. 30, displays the following peaks: $^1$H NMR (400 MHz, DMSO): δ 0.65-0.80 (4H), 1.80-2.05 (1H), 3.05-3.25 (2H), 3.40-3.80 (6H), 4.33 (2H), 6.75-6.80 (1H), 7.20-7.30 (2H), 7.30-7.35 (1H), 7.35-7.45 (1H), 7.40-7.50 (1H), 7.80-7.85 (1H), 7.85-7.95 (1H), 7.95-8.00 (1H), 8.20-8.30 (1H), and 12.60 (1H). The peak at 6.75-6.80 ppm in the $^1$H NMR spectrum corresponds to 1 proton of 3,4-dihydroxybenzoic acid. Comparison of the integration of this peak with that at 1.80-2.05 ppm, which corresponds to 1 proton of olaparib, indicates that the cocrystal has an API:coformer stoichiometry of 1:1.

Example 8

Solid-State Stability Study for the Olaparib Hydroxybenzoic Acid Cocrystals

A study was carried out to examine the physical stability of the olaparib hydroxybenzoic acid cocrystals with respect to solid form conversion or signs of decomposition over time under accelerated storage conditions. The 1:1 olaparib gentisic acid cocrystal, 2:1 olaparib gentisic acid cocrystal, 1:1 olaparib 2,4-dihydroxybenzoic acid cocrystal, 2:1 2,4-dihydroxybenzoic acid cocrystal, and the 2:1 olaparib 4-hydroxybenzoic acid cocrystal were separately stored at 40° C./75% relative humidity and 25° C./97% relative humidity for 7 days. After this time, all samples remained as white solids with no signs of deliquescence. Each sample was analysed by XRPD to observe any potential form changes and by HPLC to determine purity so as to determine any signs of decomposition. The results of the study are shown in Table 10.

TABLE 10

| COCRYSTAL | 40° C./75 RH-7 days | | 25° C./97% RH-7 days | |
|---|---|---|---|---|
| | XRPD Analysis | Purity | XRPD Analysis | Purity |
| 1:1 Olaparib Gentisic Acid | No change (as FIG. 1) | 99.70% | No change (as FIG. 1) | 99.79% |
| 2:1 Olaparib Gentisic Acid | No change (as FIG. 5) | 99.59% | No change (as FIG. 5) | 99.64% |
| 1:1 Olaparib 2,4-Dihydroxybenzoic Acid | No change (as FIG. 10) | 99.43% | No change (as FIG. 10) | 99.22% |
| 2:1 Olaparib 2,4-Dihydroxybenzoic Acid | No change (as FIG. 14) | 99.45% | No change (as FIG. 14) | 99.64% |
| 2:1 Olaparib 4-Hydroxybenzoic Acid | No change (as FIG. 19) | 99.70% | No change (as FIG. 19) | 99.69% |

Table 10 shows that after 7 days storage under accelerated conditions all the cocrystals retained their original crystalline form and that none of the olaparib hydroxybenzoic acid cocrystals of this invention undergo solid form conversion or dissociation under these conditions. All of the cocrystals showed virtually no signs of decomposition, as determined by HPLC purity analysis, when exposed to these accelerated storage conditions.

Example 9

Dissolution Studies

As described in US 2018/0113216, the oral bioavailability of olaparib is dependent on both the dissolution rate and overall solubility of the drug in the gastro-intestinal (GI) tract. US 2018/0113216 describes how olaparib has a propensity for efflux by P-gp at concentrations limiting its permeability and thus limiting its absorption from the GI tract. This efflux ratio is lowered as the concentration of drug in solution increases. Thus, to minimize this efflux issue and achieve optimal absorption and bioavailability it is essential to find a form of olaparib that has as high a dissolution rate as possible in the GI tract and that also maintains a high level of solubility over a sufficient period of time to allow the drug to be absorbed into the blood stream. A study was, therefore, carried out to examine the rate of dissolution of the 1:1 olaparib gentisic acid cocrystal, 2:1 olaparib gentisic acid cocrystal, 1:1 olaparib 2,4-dihydroxybenzoic acid cocrystal, 2:1 2,4-dihydroxybenzoic acid cocrystal, and the 2:1 olaparib 4-hydroxybenzoic acid cocrystal compared with pure crystalline olaparib form A as supplied 2-20 μm and milled crystalline olaparib form A 0.5-5 μm. The dissolution study was carried out using 50 mL simulated intestinal fluid (FaSSIF V2) at pH 6.5 (37° C.) using a quantity of each olaparib form equivalent to 25 mg olaparib. The dissolution study was carried out using the Pion inForm® instrument. Detection and quantification of olaparib was performed by in-situ UV-spectroscopy using a fibre-optic probe, allowing instantaneous data collection from the point of sample introduction. UV absorption data was converted to mg/mL (±0.2 mg/mL) using a previously determined pH dependent molar extinction coefficients to quantitate the amount of dissolved drug.

Figure 31:
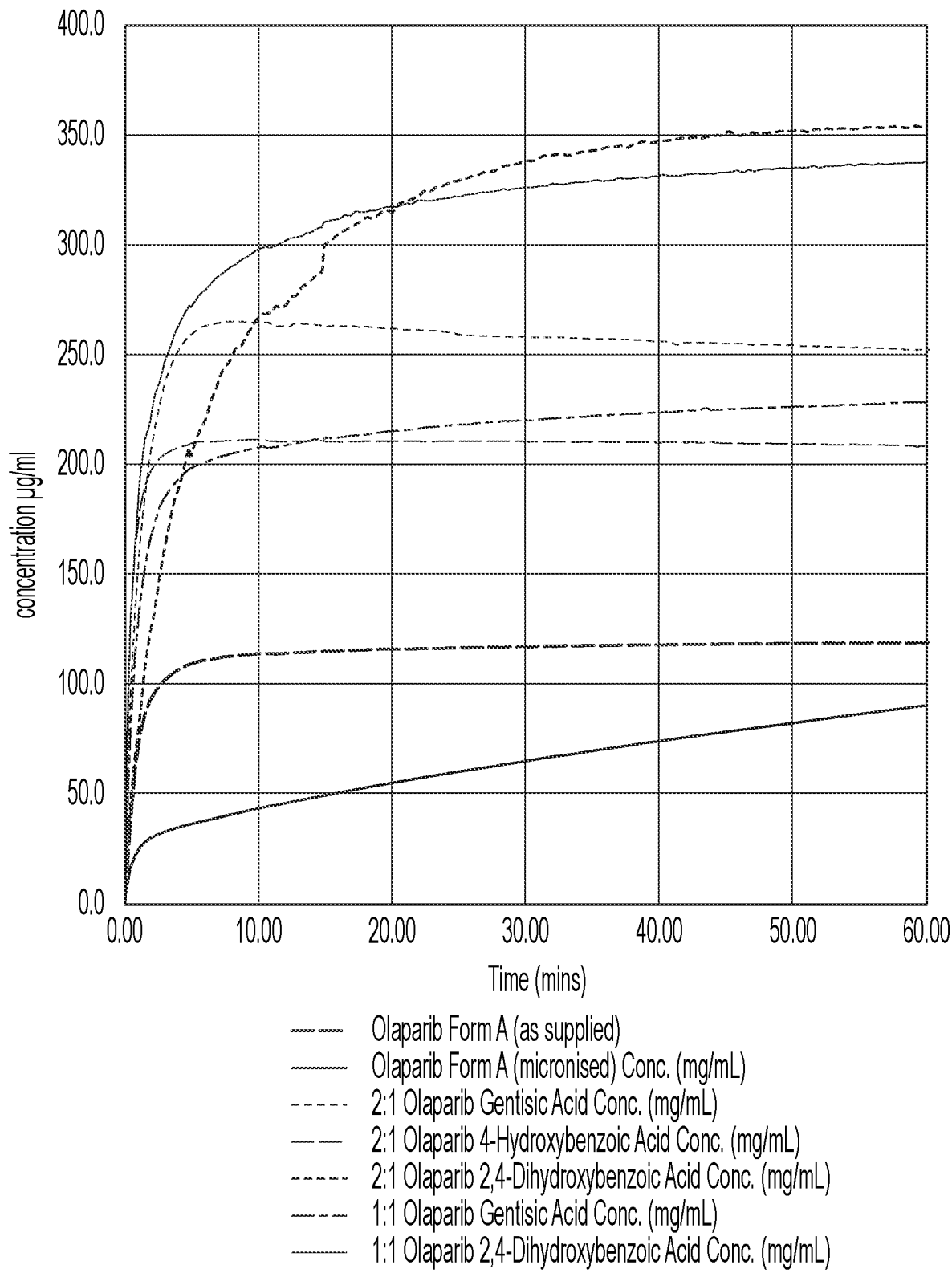
FIG. 31 shows the dissolution profiles for the 1:1 olaparib gentisic acid cocrystal, 2:1 olaparib gentisic acid cocrystal, 1:1 olaparib 2,4-dihydroxybenzoic acid cocrystal, 2:1 2,4-dihydroxybenzoic acid cocrystal, 2:1 olaparib 4-hydroxybenzoic acid cocrystal, crystalline olaparib form A as supplied, and micronized crystalline olaparib form A in FaSSIF (V2) at 37° C.

The results of the study are shown in FIG. 31. All of the hydroxybenzoic acid cocrystals of the study have a higher rate of dissolution than that of either crystalline olaparib form A as supplied or milled olaparib form A and that all of the hydroxybenzoic acid cocrystals achieve a higher level of dissolution in simulated intestinal media than olaparib form A with minimal loss of dissolution over a 60-minute time period. Although reduction in particle size by milling is a recognized method of increasing dissolution rate for poorly soluble drugs it can be seen from FIG. 31 that particle size reduction of olaparib form A results in both a lower rate of dissolution and an overall decrease in the amount of olaparib dissolved at any one timepoint over a 30-minute time period.

FIG. 32 shows an XRPD overlay of the 2:1 olaparib gentisic acid cocrystal, the 2:1 2,4-dihydroxybenzoic acid cocrystal, and the 2:1 olaparib 4-hydroxybenzoic acid cocrystal.

The claimed invention is:

1. An olaparib:hydroxybenzoic acid cocrystal, wherein the olaparib:hydroxybenzoic acid cocrystal is a 1:1 olaparib:hydroxybenzoic acid cocrystal selected from the group consisting of a 1:1 olaparib gentisic acid cocrystal, a 1:1 olaparib 2,4-dihydroxybenzoic acid cocrystal, a 1:1 olaparib salicylic acid cocrystal, and a 1:1 olaparib 3,4-dihydroxybenzoic acid cocrystal.

2. The olaparib:hydroxybenzoic acid cocrystal of claim 1, wherein the 1:1 olaparib:hydroxybenzoic acid cocrystal is the 1:1 olaparib gentisic acid cocrystal characterized by at least one of:
   a powder X-ray diffraction pattern having at least two, at least three, at least four, or all of the peaks selected from the peaks at 11.7, 13.2, 15.0, 23.5, and 25.2° 2θ±0.2° 2θ; or
   a powder X-ray diffraction pattern substantially similar to FIG. 1.

3. The olaparib:hydroxybenzoic acid cocrystal of claim 1, wherein the 1:1 olaparib:hydroxybenzoic acid cocrystal is the 1:1 olaparib 2,4-dihydroxybenzoic acid cocrystal characterized by at least one of:
   a powder X-ray diffraction pattern having at least two, at least three, at least four, or all of the peaks selected from the peaks at 3.5, 8.5, 9.4, 11.9, and 16.5° 2θ±0.2° 2θ; or
   a powder X-ray diffraction pattern substantially similar to FIG. 10.

4. The olaparib:hydroxybenzoic acid cocrystal of claim 1, wherein the 1:1 olaparib:hydroxybenzoic acid cocrystal is the 1:1 olaparib salicylic acid cocrystal characterized by at least one of:
   a powder X-ray diffraction pattern having at least two, at least three, at least four, or all of the peaks selected from the peaks at 8.4, 9.3, 12.5, 13.3, and 16.7° 2θ±0.2° 2θ; or
   a powder X-ray diffraction pattern substantially similar to FIG. 24.

5. The olaparib:hydroxybenzoic acid cocrystal of claim 1, wherein the 1:1 olaparib:hydroxybenzoic acid cocrystal is the 1:1 olaparib 3,4-dihydroxybenzoic acid cocrystal characterized by at least one of:
   a powder X-ray diffraction pattern having at least two, at least three, at least four, or all of the peaks selected from the peaks at 9.4, 11.7, 16.0, 17.4, and 19.9° 2θ+0.2° 2θ; or
   a powder X-ray diffraction pattern substantially similar to FIG. 27.

6. An olaparib:hydroxybenzoic acid cocrystal, wherein the olaparib:hydroxybenzoic acid cocrystal is a 2:1 olaparib:hydroxybenzoic acid cocrystal selected from the group consisting of a 2:1 olaparib gentisic acid cocrystal, a 2:1 olaparib 2,4-dihydroxybenzoic acid cocrystal, and a 2:1 olaparib 4-hydroxybenzoic acid cocrystal.

7. The olaparib:hydroxybenzoic acid cocrystal of claim 6, wherein the 2:1 olaparib:hydroxybenzoic acid cocrystals are characterized by a powder X-ray diffraction pattern having at least two, at least three, at least four, or all of the peaks selected from the peaks at 6.2, 10.3, 11.6, 13.5, and 17.8° 2θ±0.2° 2θ.

8. The olaparib:hydroxybenzoic acid cocrystals of claim 6, wherein the 2:1 olaparib:hydroxybenzoic acid cocrystals are characterized by an Infrared Spectrum having at least two, at least three, at least four, or all of the peaks selected from the peaks at 1014, 1222, 1243, 1435, and 1590 cm$^{-1}$±1 cm$^{-1}$.

9. The olaparib:hydroxybenzoic acid cocrystal of claim 6, wherein the 2:1 olaparib:hydroxybenzoic acid cocrystal is the 2:1 olaparib gentisic acid cocrystal characterized by at least one of:
  a powder X-ray diffraction pattern having at least two, at least three, at least four, or all of the peaks selected from the peaks at 6.1, 10.3, 11.6, 12.2, and 20.8° 2θ±0.2° 2θ; or
  a powder X-ray diffraction pattern substantially similar to FIG. 5.

10. The olaparib:hydroxybenzoic acid cocrystal of claim 6, wherein the 2:1 olaparib:hydroxybenzoic acid cocrystal is the 2:1 olaparib 2,4-dihydroxybenzoic acid cocrystal characterized by at least one of:
  a powder X-ray diffraction pattern having at least two, at least three, at least four, or all of the peaks selected from the peaks at 6.1, 11.6, 13.5, 15.7, and 19.9° 2θ±0.2° 2θ; or
  a powder X-ray diffraction pattern substantially similar to FIG. 14.

11. The olaparib:hydroxybenzoic acid cocrystal of claim 6, wherein the 2:1 olaparib:hydroxybenzoic acid cocrystal is the 2:1 olaparib 4-hydroxybenzoic acid cocrystal characterized by at least one of:
  a powder X-ray diffraction pattern having at least two, at least three, at least four, or all of the peaks selected from the peaks at 6.3, 13.6, 15.9, 19.8, and 21.6° 2θ±0.2° 2θ; or
  a powder X-ray diffraction pattern substantially similar to FIG. 19.

12. A pharmaceutical composition comprising the olaparib:hydroxybenzoic acid cocrystal of claim 1, and a pharmaceutically acceptable carrier.

13. A method of treating a disease, disorder, or condition by inhibition of the poly (ADP-ribose) polymerase (PARP), the method comprising the step of administering to a patient in need thereof a therapeutically effective amount of the olaparib:hydroxybenzoic acid cocrystal of claim 1.

14. A method of treating a disease, disorder, or condition by inhibition of the poly (ADP-ribose) polymerase (PARP), the method comprising the step of administering to a patient in need thereof a therapeutically effective amount of the pharmaceutical composition according to claim 12.

15. A method of treating cancer, fibrosis, an inflammatory condition, a neurological disease, a cardiovascular condition, an ophthalmic degenerative disease, a vascular disease, or a critical illness selected from the group of septic shock, acute lung injury (ALI), and acute liver failure, the method comprising the step of administering to a patient in need thereof a therapeutically effective amount of the olaparib:hydroxybenzoic acid cocrystal of claim 1.

16. A method of treating cancer, fibrosis, an inflammatory condition, a neurological disease, a cardiovascular condition, an ophthalmic degenerative disease, a vascular disease, or a critical illness selected from the group of septic shock, acute lung injury (ALI), and acute liver failure, the method comprising the step of administering to a patient in need thereof a therapeutically effective amount of the pharmaceutical composition according to claim 12.

17. A process for the preparation of the olaparib:hydroxybenzoic acid cocrystal of claim 1 comprising the step of slurrying a mixture of olaparib and the hydroxybenzoic acid in a solvent.

18. A process for the preparation of the olaparib:hydroxybenzoic acid cocrystal of claim 1 comprising the step of milling a mixture of olaparib and the hydroxybenzoic acid.

19. The olaparib:hydroxybenzoic acid cocrystal of claim 2, wherein the powder X-ray diffraction pattern has at least three of the peaks selected from the peaks at 11.7, 13.2, 15.0, 23.5, and 25.2° 2θ±0.2° 2θ.

20. The olaparib:hydroxybenzoic acid cocrystal of claim 3, wherein the powder X-ray diffraction pattern has at least three of the peaks selected from the peaks at 3.5, 8.5, 9.4, 11.9, and 16.5° 2θ±0.2° 2θ.

21. The olaparib:hydroxybenzoic acid cocrystal of claim 4, wherein the powder X-ray diffraction pattern has at least three of the peaks selected from the peaks at 8.4, 9.3, 12.5, 13.3, and 16.7° 2θ±0.2° 2θ.

22. The olaparib:hydroxybenzoic acid cocrystal of claim 5, wherein the powder X-ray diffraction pattern has at least three of the peaks selected from the peaks at 9.4, 11.7, 16.0, 17.4, and 19.9° 2θ±0.2° 2θ.

23. A pharmaceutical composition comprising the olaparib:hydroxybenzoic acid cocrystal of claim 6, and a pharmaceutically acceptable carrier.

24. A method of treating a disease, disorder, or condition by inhibition of the poly (ADP-ribose) polymerase (PARP), the method comprising the step of administering to a patient in need thereof a therapeutically effective amount of the olaparib:hydroxybenzoic acid cocrystal of claim 6.

25. A method of treating a disease, disorder, or condition by inhibition of the poly (ADP-ribose) polymerase (PARP), the method comprising the step of administering to a patient in need thereof a therapeutically effective amount of the pharmaceutical composition according to claim 23.

26. A method of treating cancer, fibrosis, an inflammatory condition, a neurological disease, a cardiovascular condition, an ophthalmic degenerative disease, a vascular disease, or a critical illness selected from the group of septic shock, acute lung injury (ALI), and acute liver failure, the method comprising the step of administering to a patient in need thereof a therapeutically effective amount of the olaparib:hydroxybenzoic acid cocrystal of claim 6.

27. A method of treating cancer, fibrosis, an inflammatory condition, a neurological disease, a cardiovascular condition, an ophthalmic degenerative disease, a vascular disease, or a critical illness selected from the group of septic shock, acute lung injury (ALI), and acute liver failure, the method comprising the step of administering to a patient in need thereof a therapeutically effective amount of the pharmaceutical composition according to claim 23.

28. A process for the preparation of the olaparib:hydroxybenzoic acid cocrystal of claim 6 comprising the step of slurrying a mixture of olaparib and the hydroxybenzoic acid in a solvent.

29. A process for the preparation of the olaparib:hydroxybenzoic acid cocrystal of claim 6 comprising the step of milling a mixture of olaparib and the hydroxybenzoic acid.

30. The olaparib:hydroxybenzoic acid cocrystal of claim 6, wherein the 2:1 olaparib:hydroxybenzoic acid cocrystal is hydrated.

31. The olaparib:hydroxybenzoic acid cocrystal of claim 30, wherein the 2:1 olaparib:hydroxybenzoic acid cocrystal contains up to about one water of hydration.

32. The olaparib:hydroxybenzoic acid cocrystal of claim 30, wherein the 2:1 olaparib:hydroxybenzoic acid cocrystal contains up to about two waters of hydration.

33. The olaparib:hydroxybenzoic acid cocrystal of claim 30, wherein the 2:1 olaparib:hydroxybenzoic acid cocrystal contains up to about three waters of hydration.

* * * * *